(12) United States Patent
Evans et al.

(10) Patent No.: US 10,086,110 B2
(45) Date of Patent: Oct. 2, 2018

(54) MULTIPURPOSE MEMBRANES, METHODS FOR FORMING, AND APPLICATIONS THEREOF

(71) Applicant: THE CLEVELAND CLINIC FOUNDATION, Cleveland, OH (US)

(72) Inventors: Peter J. Evans, Cleveland, OH (US); Jim Trickett, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/067,120

(22) Filed: Oct. 30, 2013

(65) Prior Publication Data

US 2014/0121640 A1 May 1, 2014

Related U.S. Application Data

(60) Provisional application No. 61/752,492, filed on Jan. 15, 2013, provisional application No. 61/720,126, filed on Oct. 30, 2012.

(51) Int. Cl.
*A61L 26/00* (2006.01)
*A61L 27/36* (2006.01)
*A61L 24/00* (2006.01)

(52) U.S. Cl.
CPC ........ *A61L 26/0057* (2013.01); *A61L 24/0005* (2013.01); *A61L 27/3616* (2013.01); *A61L 26/0042* (2013.01); *A61L 2430/32* (2013.01)

(58) Field of Classification Search
CPC ............ A61L 26/0057; A61L 27/3616; A61L 24/0005; A61L 2430/32

USPC ......................................................... 424/529
See application file for complete search history.

(56) References Cited

U.S. PATENT DOCUMENTS

| | | | |
|---|---|---|---|
| 4,969,880 A * | 11/1990 | Zamierowski | ................ 604/305 |
| 6,133,325 A * | 10/2000 | Schwartz | ............. A61L 31/041 |
| | | | 514/54 |
| 6,197,194 B1 | 3/2001 | Whitmore | |
| 6,730,120 B2 * | 5/2004 | Berg | ..................... A61L 33/007 |
| | | | 604/265 |
| 7,348,411 B2 | 3/2008 | Petrescu | |
| 2008/0190857 A1 | 8/2008 | Beretta et al. | |

(Continued)

FOREIGN PATENT DOCUMENTS

| | | | |
|---|---|---|---|
| WO | WO-0004821 A1 * | 2/2000 | .............. A61B 5/00 |
| WO | WO-03035115 A2 * | 5/2003 | ....... A61B 17/00491 |

(Continued)

OTHER PUBLICATIONS

PCT Communication Relating to the Results of the Partial International Search, dated Feb. 7, 2014, pp. 3-4.

*Primary Examiner* — Sean C Barron
(74) *Attorney, Agent, or Firm* — Farolli, Sundheim, Covell & Tummino LLP

(57) ABSTRACT

One aspect of the present disclosure relates to a method for forming a multipurpose membrane in vivo. One step of the method includes obtaining a blood component. Next, a vacuum assembly is operated to remove substantially all of the liquid from the blood component and thereby form a concentrated, substantially dehydrated blood component. The substantially dehydrated blood component is then formed into a non-coagulated injectable composition and administered to a wound of a subject.

11 Claims, 18 Drawing Sheets

(56) References Cited

U.S. PATENT DOCUMENTS

| | | | |
|---|---|---|---|
| 2008/0199513 A1* | 8/2008 | Beretta | A61B 17/00491 424/443 |
| 2008/0286329 A1 | 11/2008 | Campbell et al. | |
| 2009/0018313 A1 | 1/2009 | Shanbrom | |
| 2011/0015565 A1 | 1/2011 | Hursey | |
| 2011/0020196 A1 | 1/2011 | Grippi et al. | |
| 2012/0003324 A1 | 1/2012 | Campbell et al. | |

FOREIGN PATENT DOCUMENTS

| | | |
|---|---|---|
| WO | 2004048449 A2 | 6/2004 |
| WO | 2006102488 A1 | 9/2006 |

* cited by examiner

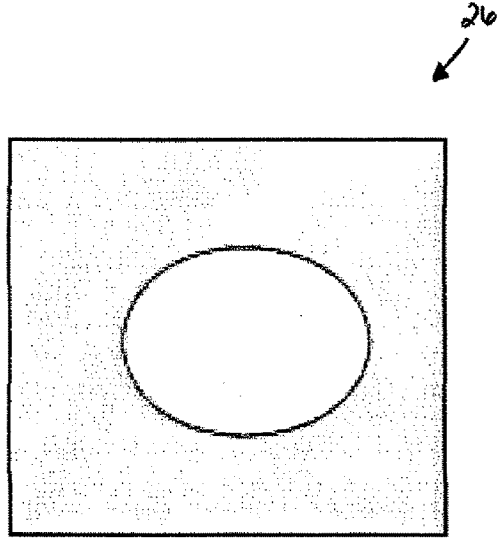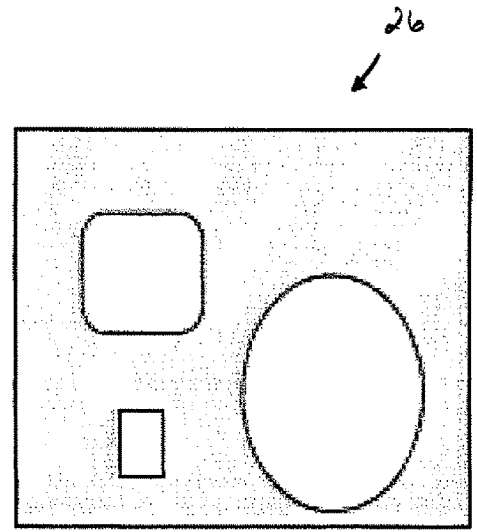
Fig. 3A　　　　　　　　　　　Fig. 3B
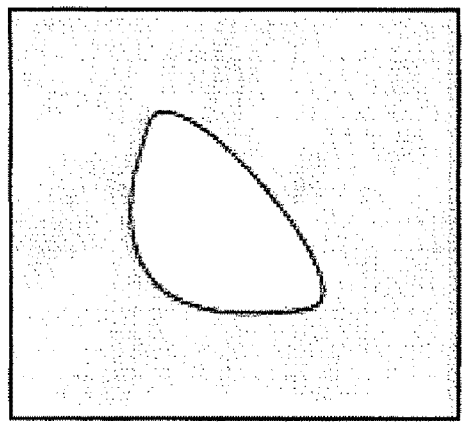
Fig. 3C

MULTIPURPOSE MEMBRANES, METHODS FOR FORMING, AND APPLICATIONS THEREOF

RELATED APPLICATIONS

This application claims the benefit of U.S. Provisional Patent Application Ser. No. 61/720,126, filed Oct. 30, 2012, and 61/752,492, filed Jan. 15, 2013, the entirety of which is hereby incorporated by reference for all purposes.

TECHNICAL FIELD

The present disclosure relates generally to wound therapy and, more particularly, to multipurpose membranes and related methods for forming and using the membranes.

BACKGROUND

In some circumstances, a patient's body is unable to heal a wound on its own. Many factors can cause a particular wound to become a hard-to-heal wound, such as the size and severity of the wound, the patient's age, illness, the location of the wound, the nutritional intake of the patient, etc. One example of a hard-to-heal wound is an injury to a peripheral nerve. Following peripheral nerve injury, for example, surgical nerve repair (neurorrhaphy) is typically done by suture or fibrin glue, which causes the nerves to regenerate across the repair site in an exuberant manner (e.g., with regenerating axons aberrantly growing out from the repair site). Simultaneously, a classic tissue repair cascade is underway with fibroblasts laying down collagen to bind the nerve ends and any damaged surrounding tissue.

Typically, the response is excessive and profuse scarring appears within the nerve repair site and around the nerve. The excessive response creates a compressive sheath and adherence to muscle and other subcutaneous tissue, thereby preventing essential gliding of the nerve and blocking regeneration. Additionally, aberrant regenerating neurites escape the repair site. The result is compromised regeneration with fewer axons heading down the distal nerve stump, as well as a painful adherent neuroma. Revision surgery to help improve poor nerve function centers on dissecting scar off the nerve (neurolysis) to help promote better blood supply and nerve gliding. Unfortunately, the scarring response occurs again and compromises this attempt.

SUMMARY

The present disclosure relates generally to wound therapy and, more particularly, to multipurpose membranes and related methods for forming and using the membranes.

One aspect of the present disclosure relates to a method for forming a multipurpose membrane in vivo. One step of the method includes obtaining a blood component. Next, a vacuum assembly is operated to remove substantially all of the liquid from the blood component and thereby form a concentrated, substantially dehydrated blood component. The substantially dehydrated blood component is then formed into a non-coagulated injectable composition and administered to a wound of a subject.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 3A-E are a series of schematic illustrations showing alternative configurations of the mold in FIGS. 2A-E;

FIG. 4A-1, FIG. 4A-2 and FIG. 4A-3 is a series of schematic illustrations showing a wicking assembly and a related series of steps for dehydrating a coagulated blood component according to another aspect of the present disclosure;

DETAILED DESCRIPTION

Definitions

Figure 1:
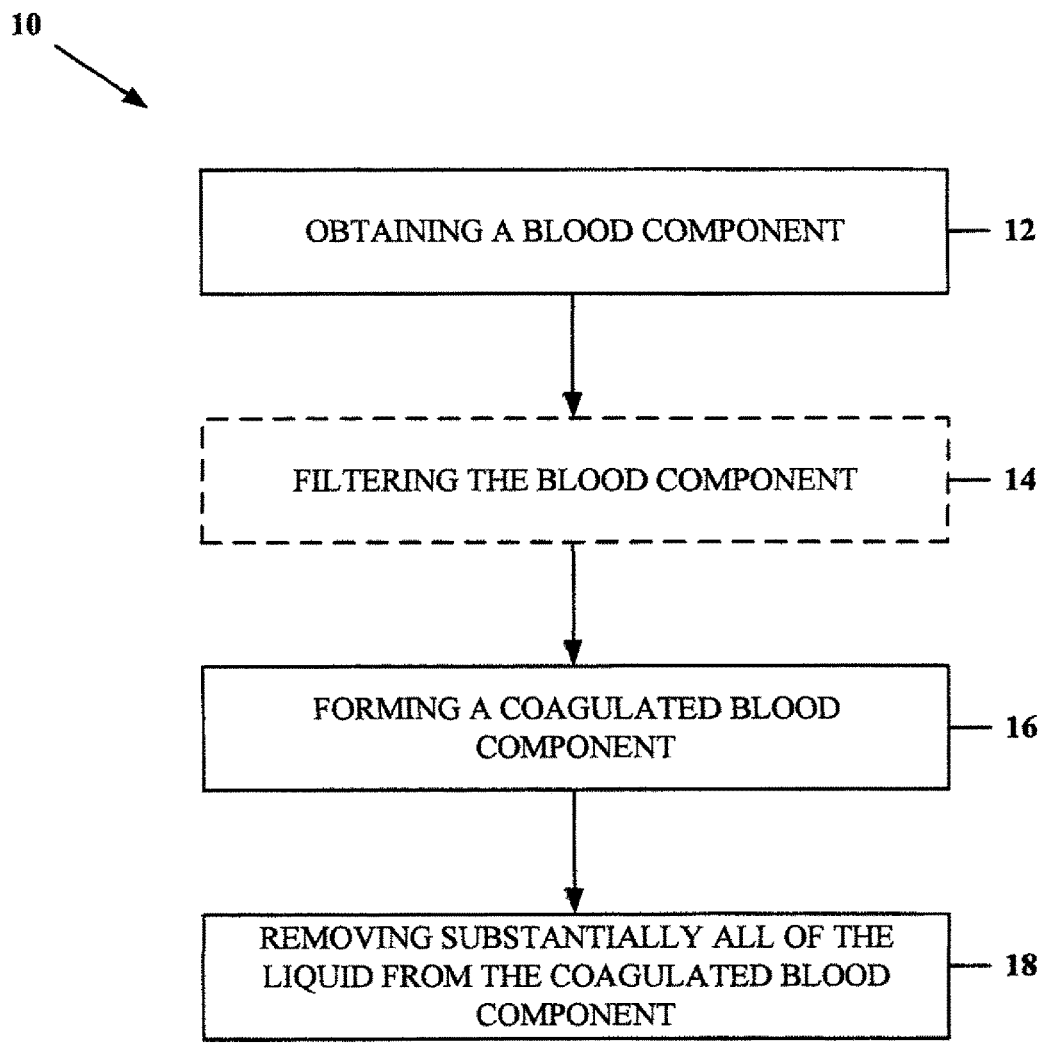
FIG. 1 is a process flow diagram illustrating a method for forming a multipurpose membrane according to one aspect of the present disclosure.

Unless defined otherwise, all technical and scientific terms used herein have the same meaning as is commonly understood by one of skill in the art to which the present disclosure pertains.

In the context of the present disclosure, the term "tissue" can refer to an aggregation of similarly specialized cells united in the performance of a particular function. "Tissue" can encompass all types of biological tissue including both hard and soft tissue, such as connective tissue (e.g., hard forms, such as osseous tissue or bone), as well as other muscular, skeletal or nerve tissue.

As used herein, the term "blood component" can refer to any composition that includes at least one red blood cell (RBC) and/or is derived from a source of RBCs.

As used herein, the term "blood" can generally refer to whole blood or any fraction thereof, such as plasma or serum.

As used herein, the term "whole blood" can refer to a body fluid (technically a tissue) that is composed of blood cellular components suspended in plasma. Blood cellular components include RBCs, white blood cells (including both leukocytes and lymphocytes) and platelets (also called thrombocytes).

As used herein, the term "plasma" can refer to the fluid portion of human blood that has been collected, stabilized against clotting, and separated from RBCs. Plasma may be obtained from whole blood. Blood plasma is essentially an aqueous solution containing about 92% water, about 8% blood plasma proteins (e.g., serum albumin, blood clotting factors, immunoglobulins (antibodies)), various other proteins, electrolytes (e.g., sodium and chloride), hormones, xymogens, proteases, protease inhibitors, and trace amounts of other materials.

As used herein, the term "serum" can refer to blood plasma from which the clotting proteins have been removed, i.e., without fibrinogen and other clotting factors. A large percentage of the proteins remaining can include albumin and immunoglobulins.

As used herein, the terms "platelet-rich plasma" or "PRP" can refer to blood plasma having an increased concentration of platelets (typically after removal of RBCs and/or white blood cells) as compared to the concentration of platelets in the blood plasma at a baseline. In one example, PRP can be prepared by centrifugation and may have at least 250,000 platelets per microliter.

As used herein, the terms "platelet-poor plasma" or "PPP" can refer to a portion of a plasma fraction of blood having a decreased concentration of platelets as compared to the concentration of platelets in the blood plasma at a baseline. In some instances, fresh frozen plasma may be the same as PPP.

As used herein, the term "allogeneic" when used in the context of blood can refer to blood that is taken from different subjects within the same species.

As used herein, the term "autologous" when used in the context of blood can refer to blood that is taken from a subject to be treated.

As used herein, the term "subject" can refer to any warm-blooded organism including, but not limited to, humans, pigs, rats, mice, dogs, goats, sheep, horses, monkeys, apes, rabbits, cattle, etc.

Overview

The present disclosure relates generally to wound therapy and, more particularly, to multipurpose membranes and related methods for forming and using the membranes. In some aspects, the present disclosure utilizes a blood component (e.g., whole blood or its components, such as PRP or PPP) to form a membrane that is strong enough to accommodate sutures and remain in vivo long enough to augment the initial healing response (e.g., prevent scarring and promote tissue regeneration and/or revascularization). As described in more detail below, the present disclosure advantageously provides: (1) a method for forming a multipurpose membrane (e.g., an autologous membrane) that can be customized to any wound site and is strong enough to hold sutures; (2) a membrane whose absorption rate can be altered by the amount and concentration of certain therapeutic additives (e.g., anti-fibrinolytic agents); (3) a membrane whose biological properties can be varied or customized based on its tissue source(s) (e.g., whole blood, blood products, fat, muscle, bone marrow, etc.); and (4) a membrane that can be used as a delivery device by, for example, impregnating the membrane with one or more therapeutic additives (e.g., antibiotics, drugs, growth factors, etc.) to promote wound healing and/or prevent infection.

Multipurpose membranes of the present disclosure can possess one or more of the following desirable characteristics: biocompatibility with the host or subject; the ability to degrade in relation to tissue regeneration; the inclusion of therapeutic additives (e.g., growth factors) in the membrane, which may help to produce therapeutic results and speed wound recovery; the ability to easily engineer the mechanical properties (e.g., elasticity) of the membrane; the ability to easily shape the membrane at a time and a place where the membrane will be fabricated and/or clinically applied (e.g., in an operating room, a battlefield, etc.); the ability to modulate the physiological response to the implanted membrane by incorporating other materials or therapeutic additives into the base membrane; and the ability to prevent adhesions to implanted medical devices, such as grafts, pace makers, breast implants, orthopedic devices, etc.

Formation Methods

Figures 1, 4A:
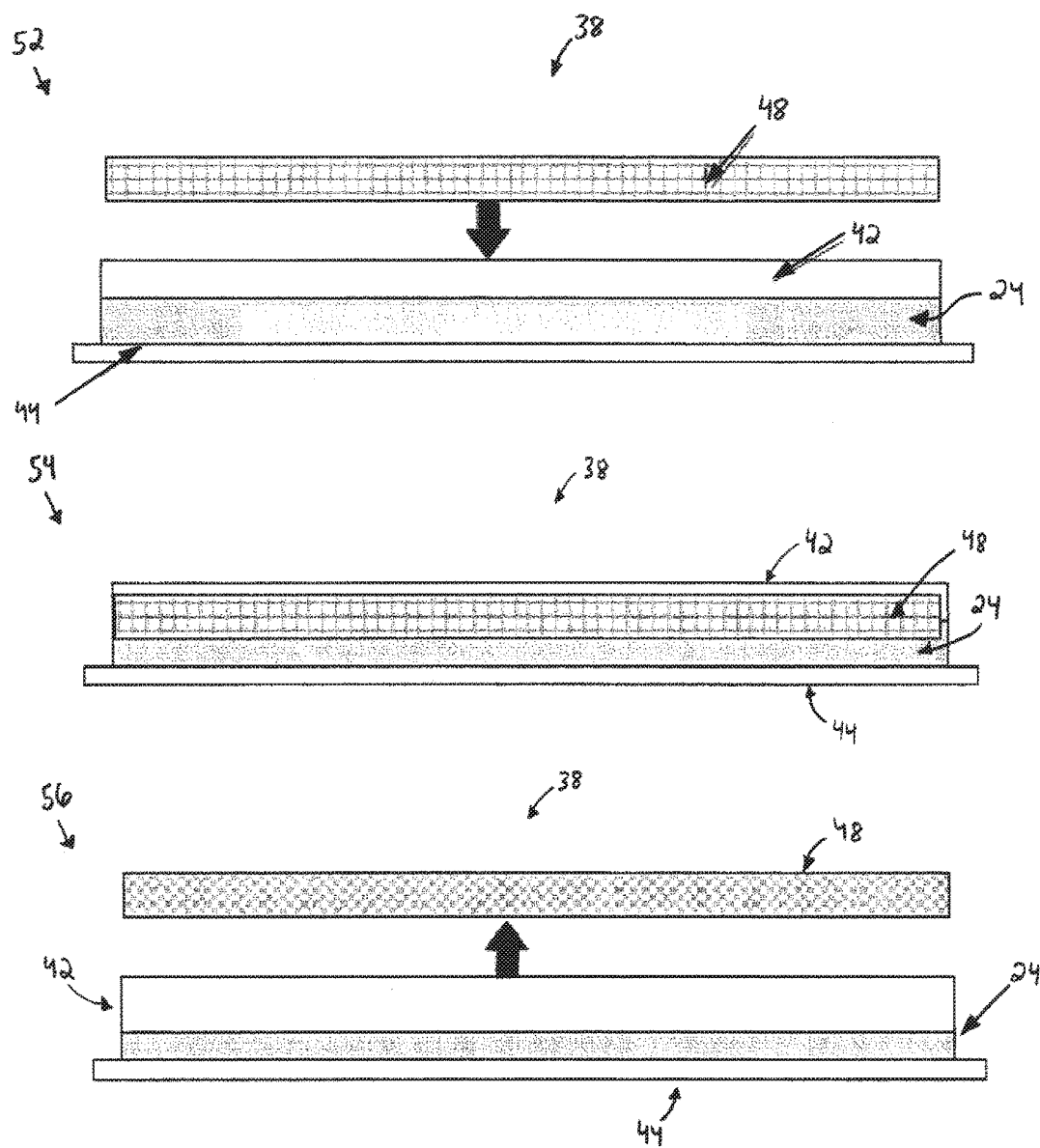
Figures 2, 4A:
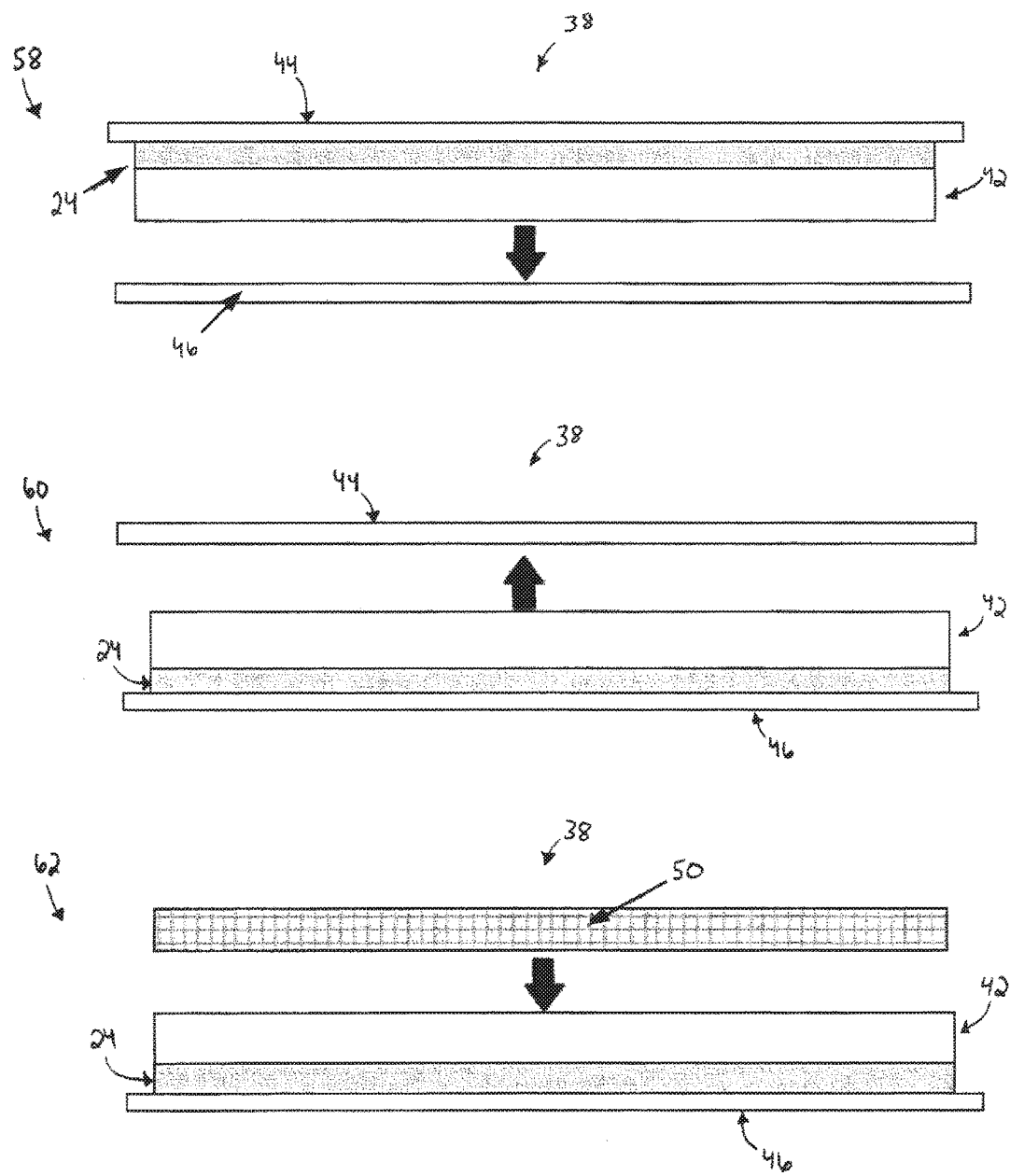
Figures 3, 4A:
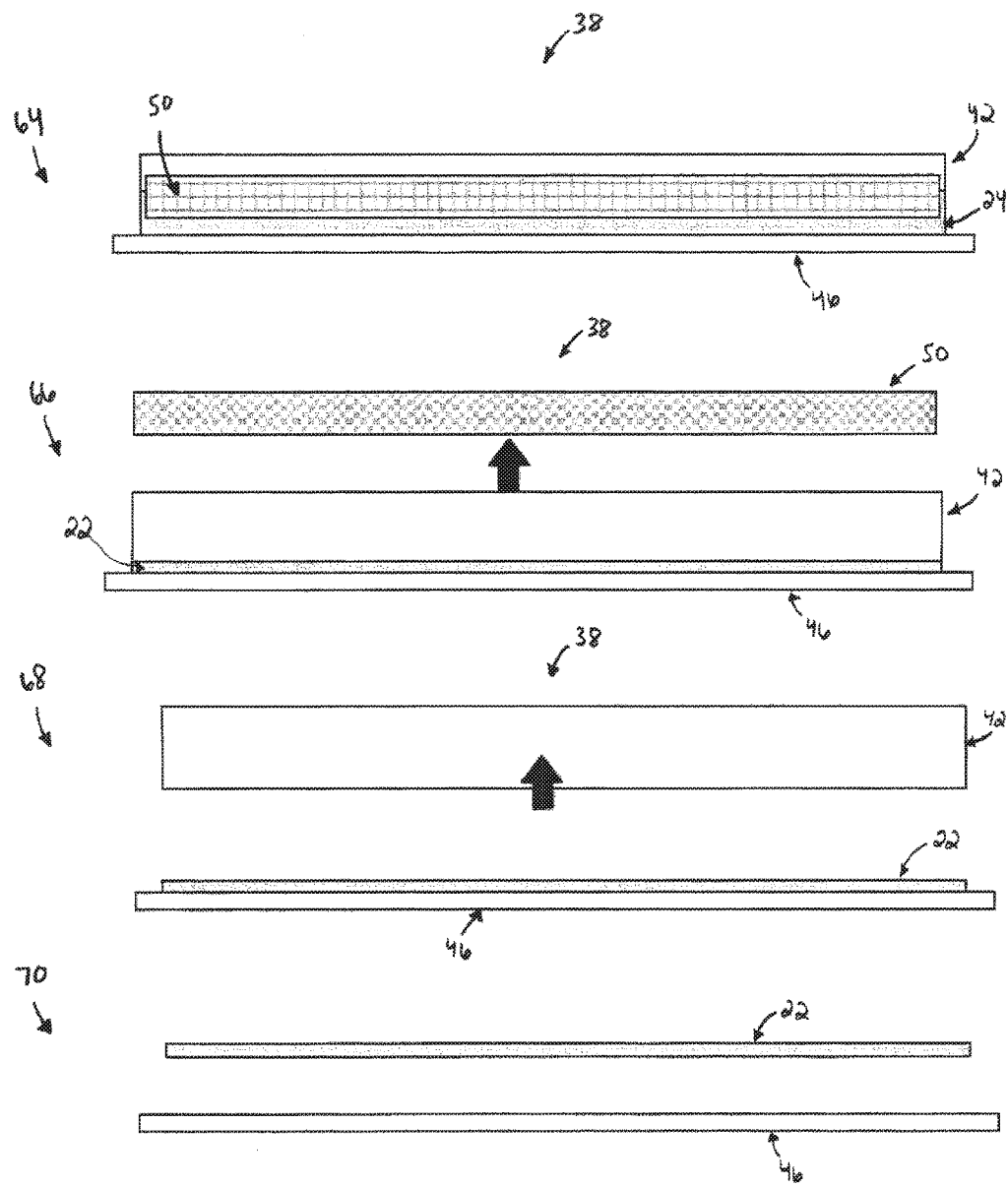

One aspect of the present disclosure is illustrated in FIG. 1 and includes a method 10 for forming a multipurpose membrane 22 (FIG. 4A). Membranes 22 formed by the method 10 can find use in a variety of biological applications, which are discussed in detail below. Unlike conventional methods used to form blood-derived membranes, which are typically time-consuming, performed in a laboratory, and require cooler temperatures, the method 10 of the present disclosure can be performed immediately prior to and/or during surgery at or about room temperature. Consequently, there is no need to perform the method 10 in a laboratory apart from the surgical suite or clinic, which significantly decreases the time, equipment, and personnel needed to form the multipurpose membrane 22. In fact, unlike conventional techniques used to form blood-derived membranes, which may take several hours to complete, the method 10 of the present disclosure advantageously allows formation of a multipurpose membrane 22 in less than about 30 minutes.

In another aspect, the method 10 can begin by obtaining a blood component (e.g., from a subject) at Step 12. The blood component can be obtained from one or a combination of biological sources, such as whole blood (or a component thereof), bone marrow, muscle, fat, etc. In one example, the blood component can comprise a volume of whole blood. Whole blood can be collected at any time, such as prior to surgery. Thus, in some instances, whole blood used in the method 10 can be autologous. In other instances, whole blood used in the method 10 can be allogeneic. In further instances, the whole blood can be obtained from commercial sources, such as blood banks. These preparations can be derived from units of human blood (or blood plasma), which have been tested to elicit no antigen-antibody reaction (e.g., non-reactive for antibodies to hepatitis B surface antigen (HBsAg) and hepatitis C (HCV) antibody, and negative for antibodies to HIV-1 and HIV-2). All units of blood used for the method 10 will be certified free of pathogens. To reduce the potential risk of transmission of infectious agents, blood preparations may be treated with an organic solvent/detergent mixture, such as tri(n-butyl)/phosphate/polysorbate designed to inactivate enveloped viruses, such as HIV, hepatitis B and HCV. The inactivation and removal of viruses can be enhanced by nanofiltration. In some instances, plasma can be prepared by pasteurization of a liquid plasma fraction.

In one example, the blood component (e.g., whole blood) can be processed to obtain a platelet component (not shown). A "platelet component" component can include any blood component (e.g., plasma) that contains at least one platelet and is substantially free of RBCs and/or white blood cells. In some instances, a platelet component can be obtained by conventional methods (e.g., centrifugation, sedimentation, filtration, etc.). For example, the platelet component can be obtained by centrifuging the volume of whole blood for a desired period of time at a desired RPM. Following centrifugation, for example, the supernatant plasma can be separated from the centrifuged cells by conventional techniques (e.g., by passing the supernatant plasma through a suitable filter, such as a microporous membrane). In some instances, a volume of whole blood can be spun down to obtain PRP. In other instances, a volume of whole blood can be spun down to obtain PPP. The choice of whether the platelet component will comprise PRP or PPP can be based upon the intended biological application of the multipurpose membrane 22. It will be appreciated that other methods, such as apheresis may be used to collect plasma from a subject without having to collect whole blood.

At Step 14, the blood component is optionally subjected to filtration. In some aspects, the blood component can be subjected to ultrafiltration. Generally, ultrafiltration includes a type of filtration in which hydrostatic pressure forces a liquid against a semi-permeable membrane. Suspended solids and solutes of high molecular weight are typically retained during ultrafiltration, while water and low molecular weight solutes can pass through the ultrafiltration membrane. Different types of membranes may be used for ultrafiltration, such as spiral wound modules, tubular membranes, and hollow fiber membranes. Various types of ultrafiltration membranes are commercially available for filtering plasma. Examples of commercially available ultrafiltration membranes that may be used as part of the method 10 are known by those of skill in the art.

After obtaining the blood component, the blood component can be contacted with one or more coagulation activators to form a coagulated blood component 24 (FIG. 4A) (Step 16). In some instances, the platelet component can be contacted with one or more coagulation activators so that the blood component (e.g., a platelet component) is at least partially clotted. In other instances, the blood component can be contacted with one or more coagulation activators so that the blood component is essentially fully clotted. Coagulation activators can include any one or combination of agents or substances that causes a sol or liquid, such as blood to coagulate. Examples of coagulation activators can include alpha-2-antiplasmin, alpha-1-antitrypsin, alpha-2-macroglobulin, aminohexanoic acid, aprotinin, a source of calcium ions, calcium alginate, calcium-sodium alginate, casein kinase II, chitin, chitosan, collagen, cyanoacrylates, epsilon-aminocaproic acid, Factor XIII, fibrin, fibrin glue, fibrinogen, fibronectin, gelatin, living platelets, methacrylates, PAI-1, PAI-2, plasmin activator inhibitor, plasminogen, platelet agonists, protamine sulfate, prothrombin, an RGD peptide, sphingosine, a sphingosine derivative, thrombin, thromboplastin, and tranexamic acid. One skilled in the art can readily determine the appropriate amount(s) of coagulation activator(s) and suitable conditions for clotting.

Figure 2A:
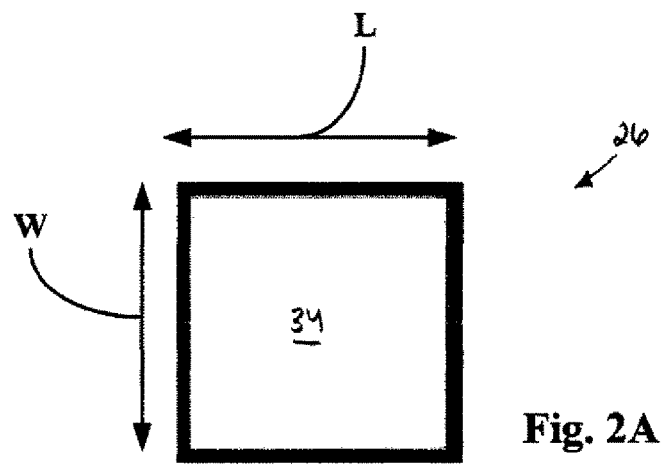
FIGS. 2A-E are a series of schematic illustrations showing a mold for use in the method of FIG. 1.
Figure 2B:
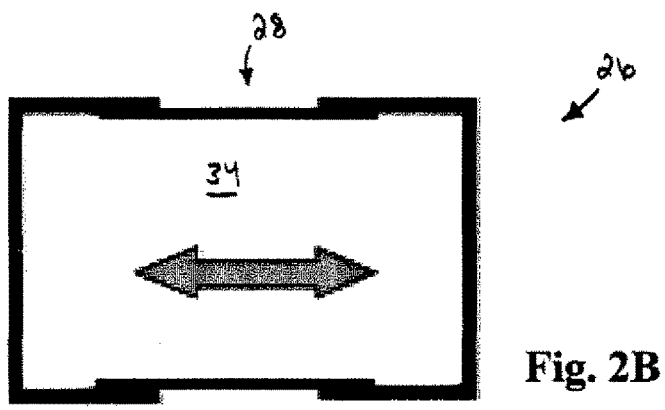
Figure 2C:
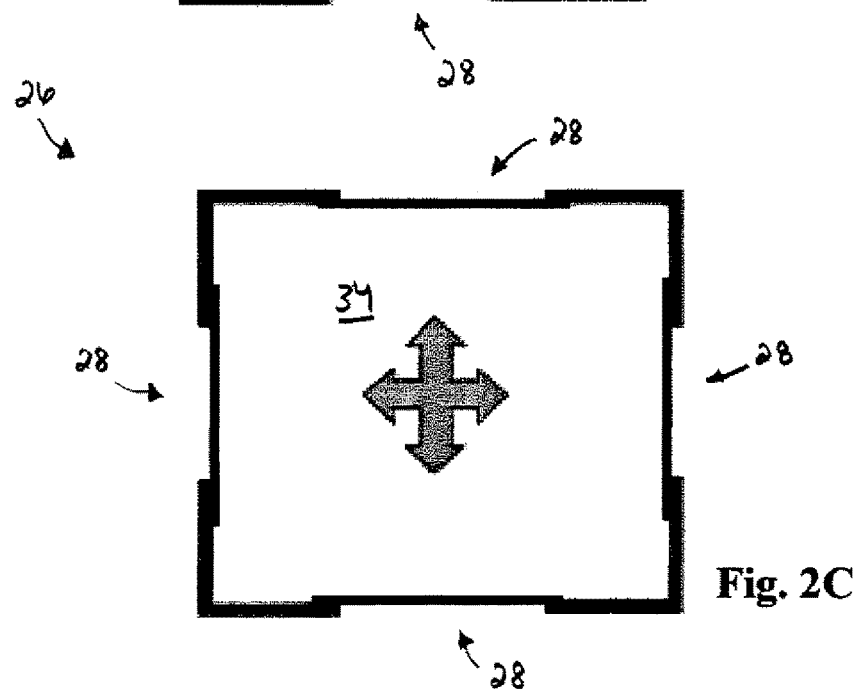
Figure 2D:
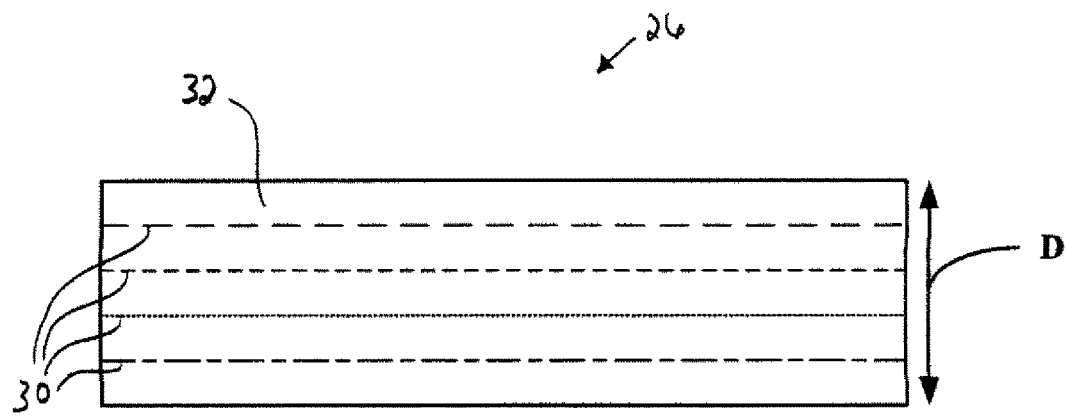
Figure 2E:
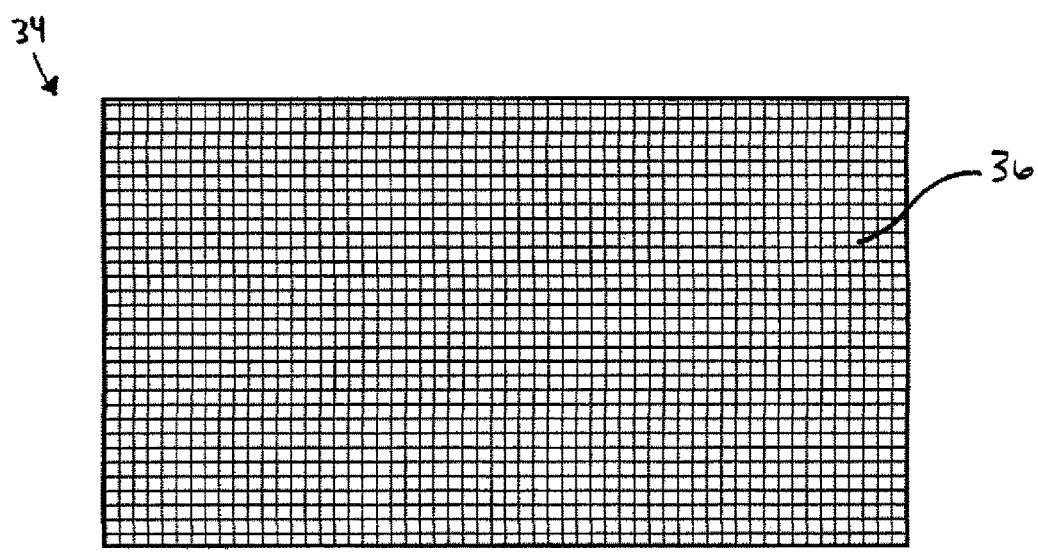
Figure 3D:
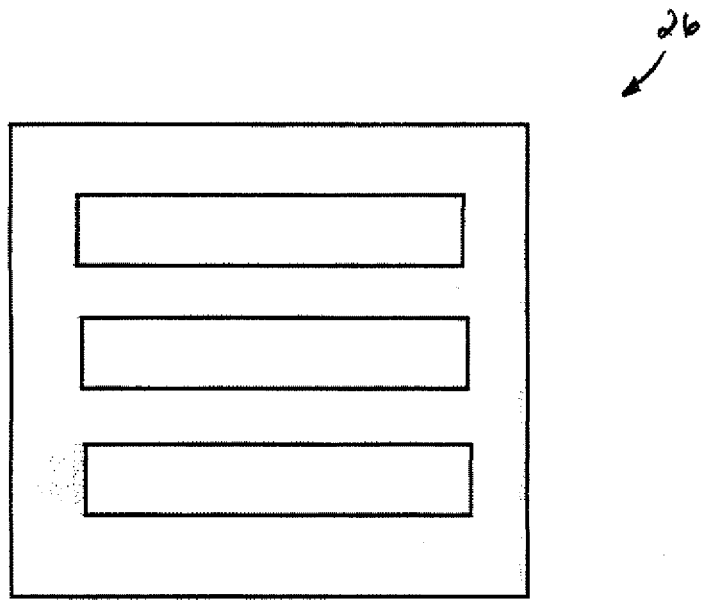
Figure 3E:
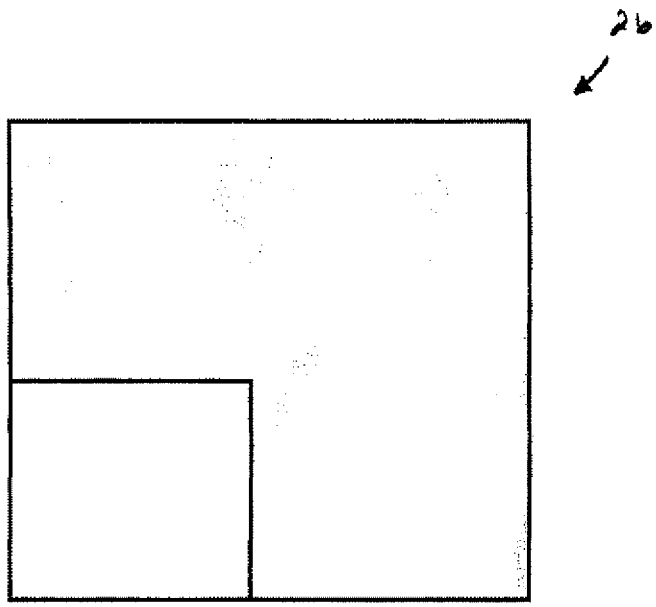

Either prior to or following contact of the blood component with the coagulation activator(s), the blood component can be disposed (e.g., poured or manually placed) in a mold 26 (FIGS. 2A-E). The mold 26 can comprise any structure that allows the dimensions (e.g., length, width, thickness) and properties (e.g., surface texture, porosity, water content, etc.) of the blood component to be selectively adjusted so that the membrane 22 formed by the method 10 is specifically configured and shaped for a particular biological application. In one example, the mold 26 (FIG. 2A) can comprise a box-shaped device having a length L, width W and depth D (FIG. 2D). The mold 26 can be formed from a flexible or solid material, such as silicon. One or a series of shapes (FIGS. 3A-E) can be formed in the mold 26 by, for example, die cutting or manual cutting. As discussed in more detail below, the mold 26 can be configured so that a liquid (e.g., water) can be removed from a coagulated blood component 24.

As shown in FIGS. 2B-C, the mold 26 can include one or more adjustment mechanisms 28 (not shown in detail) that allow the length L and/or width W of the mold to be increased or decreased. Advantageously, the adjustability of the mold 26 imparted by the adjustment mechanism(s) reduces waste associated with membrane 22 formation by allowing the dimensions of the membrane to be pre-sized or customized prior to final formation and use. The mold 26 (FIG. 5D) can additionally include one or more graduated indices 30 (e.g., disposed on an outer wall 32 thereof). Each of the graduated indices 30 can represent a depth D (e.g., in cm), which corresponds to a desired membrane thickness. Additionally, the mold 26 can include a base portion 34 (FIG. 2E) having a surface 36 configured similar to graph paper. In one example, the surface 36 can include grid lines that define equally-sized segments, which correspond to a particular numerical value (e.g., mm, cm, etc.). The surface 36 can be smooth or, in some instances, include a raised or depressed pattern (e.g., dimples) to impart the membrane 22 with a desired surface texture. Although a box-shaped mold 26 is shown in FIGS. 2A-E, it will be appreciated that the mold can have any other desired shape or configuration (e.g., rectangular, elliptical, circular, etc.).

Following Step 16, a wicking assembly 38 (FIGS. 4A-B) or a vacuum assembly 40 (FIGS. 5A-D) can be operated to remove a desired amount of liquid (e.g., water) from the coagulated blood component 24 (Step 18). In some instances, an amount of liquid (e.g., water) can be removed from the coagulated blood component 24 so that the liquid content of the coagulated blood component is about 50%, about 40%, about 30%, about 20%, or about 10% or less. In other instances, an amount of liquid (e.g., water) can be removed from the coagulated blood component 24 so that the coagulated blood membrane is substantially dehydrated, e.g., having a water content of less than about 10%, less than about 5%, or less than about 1%. One skilled in the art will appreciate that the coagulated blood component 24 can be dehydrated to a desired liquid (e.g., water) content based on the intended biological application of the membrane 22.

Figure 4B:
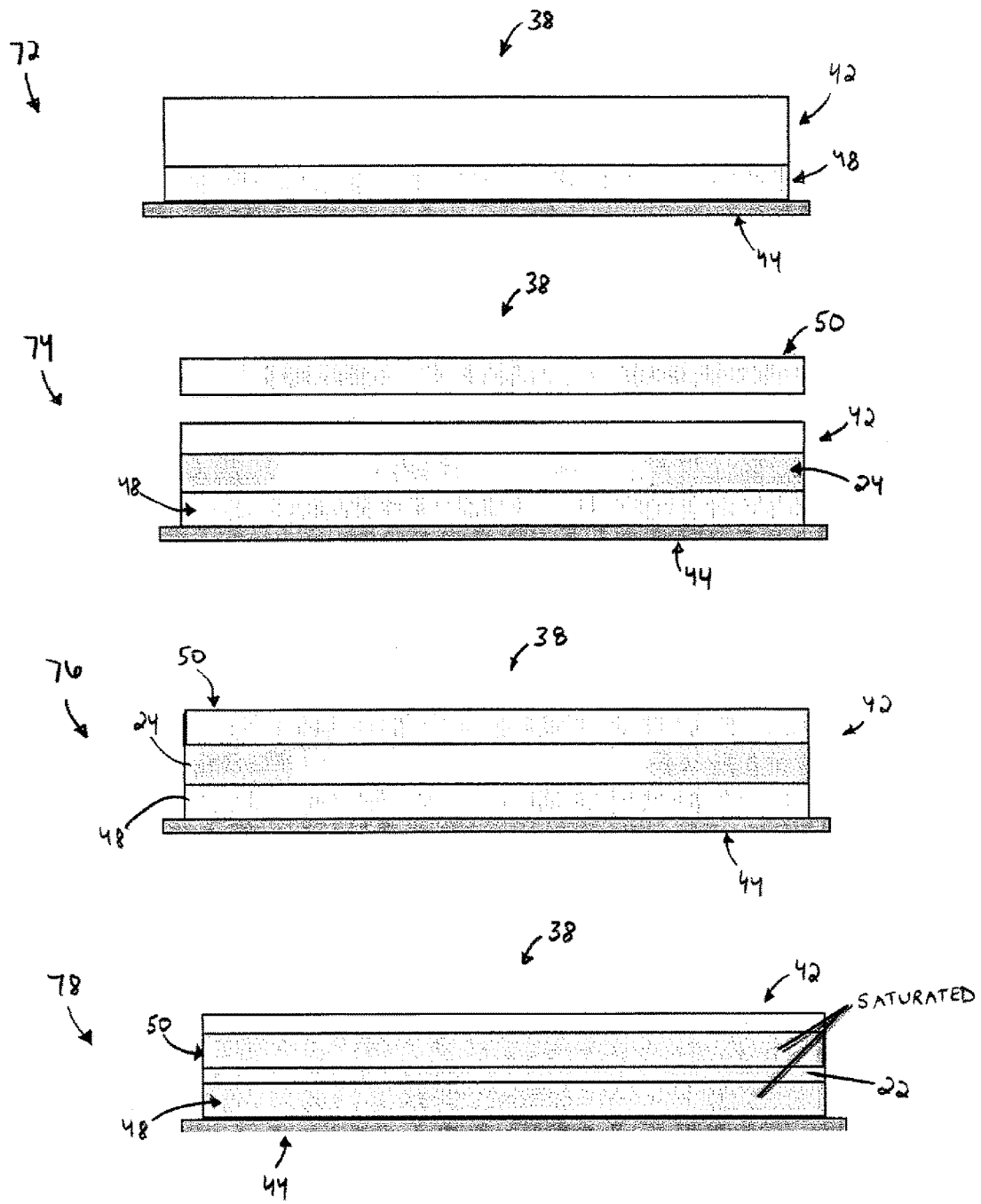
FIG. 4B is a series of schematic illustrations showing an alternative wicking assembly and for dehydrating a coagulated blood component according to another aspect of the present disclosure.

In another aspect, a desired amount of liquid (e.g., water) can be removed from the coagulated blood component 24 using a wicking assembly 38 (FIGS. 4A-B). The wicking assembly 38 can generally comprise a containing structure 42 (e.g., a ring), a first base member 44 (e.g., an elastomeric sheet), a second base member 46 that is identically or similarly configured as the first base member, a first absorbent material 48, and a second absorbent material 50. Each of the first and second absorbent materials 48 and 50 can be shaped and configured to snugly fit within the containing structure 42. Although the containing structure 42 is shown as a ring in FIG. 4A, it will be appreciated that the containing structure can have any desired shape depending upon the intended biological application of the membrane 22.

At Step 52, the containing structure 42 is placed on top of (and secured to) the first base member 44 to form a sealed cavity. The coagulated blood component 24 is then disposed within the cavity, followed by placement of the first absorbent material 48 on top of the exposed portion of the coagulated blood component (Step 54). The first absorbent material 48 remains in contact with the coagulated blood component 24 until the first absorbent material 48 is substantially saturated. Once the first absorbent material 48 is substantially saturated, the first absorbent material is removed from contact with the coagulated blood component 24 (Step 56). Following removal of the first absorbent material 48, the first base member 44 (along with the containing structure 42) is flipped over and placed on top of the second base member 46 (as shown in Step 58). After placing the containing structure 42 into contact with the second base member 46, the first base member 44 is removed from contact with the containing structure (Step 60). Next, the second absorbent material 50 is placed into contact with the exposed surface of the coagulated blood component 24 (Step 62), followed by placement of the first base member 44 over the second absorbent material (Step 64). The second absorbent material 50 is then allowed to remain in contact with the coagulated blood component 24 until the second absorbent material is substantially saturated. After the second absorbent material 50 has become saturated, the second absorbent material and the containing structure 42 are removed from contact with the coagulated blood component 24 and the second base member 46, respectively (Steps 66-68). At Step 70, the membrane 22 is formed and ready for a desired biological application.

FIG. 4B illustrates an alternative technique using the wicking assembly 38 to dehydrate the coagulated blood component 24. At Step 72, a containing structure 42 is securely placed atop a first base member 44 to form a cavity. A first absorbent material 48 is then placed inside the cavity. Next, the coagulated blood component 24 is disposed on top of the first absorbent material 48 inside of the cavity (Step 74). At Step 76, a second absorbent material 50 is placed atop the exposed surface of the coagulated blood component 24. The coagulated blood component 24 then remains in the wicking assembly 38 (Step 78) for a desired period of time, i.e., until the coagulated blood component obtains the desired liquid (e.g., water) content. Once the coagulated blood component 24 obtains the desired liquid (e.g., water) content, the wicking assembly 38 can be disassembled so that the resultant membrane 22 is ready for an intended biological application.

Figure 4C:
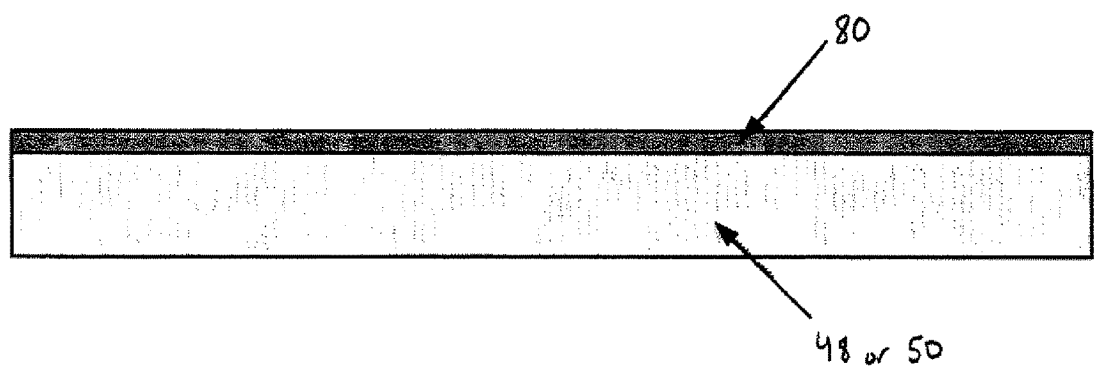
FIG. 4C is a schematic illustration showing an ultrafiltration membrane layered on top of an absorbent wicking material for use with the wicking assemblies in FIGS. 4A-B.

It will be appreciated that the absorbent materials (e.g., the first and second absorbent materials 48 and 50) used as part of the wicking assembly 38 can be configured as shown in FIG. 4C. For example, one or both of the first and second absorbent materials 48 and 50 can include a membrane 80 (e.g., an ultrafiltration membrane) disposed thereon. The addition of a membrane 80 to one or both of the first and second absorbent materials 48 and 50 can selectively inhibit certain biological materials from being transferred (e.g., by bulk diffusion) when liquid (e.g., water) is wicked between the membrane 80 and coagulated blood component 24.

Figure 5A:
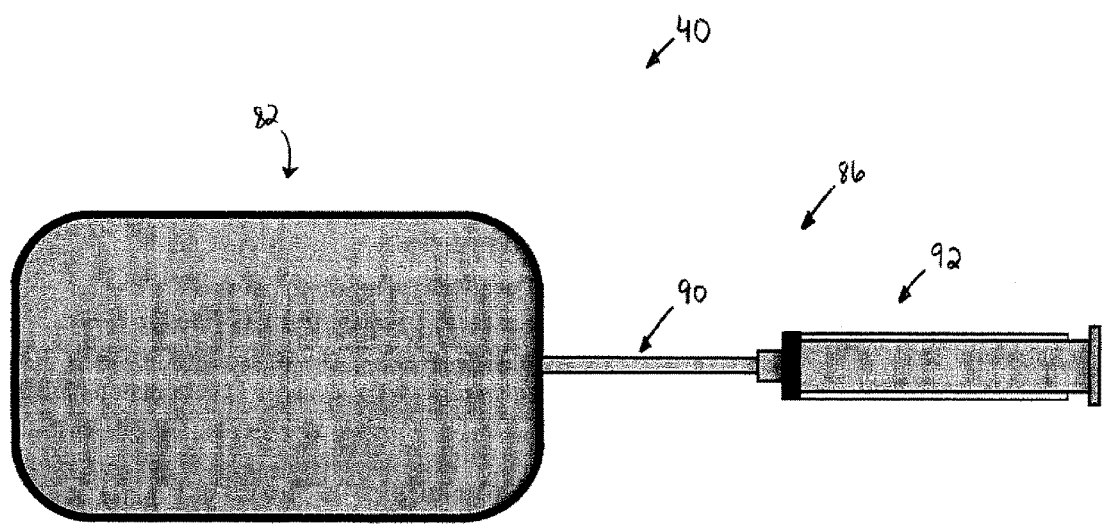
FIGS. 5A-D are a series of schematic illustrations showing a vacuum assembly (FIGS. 5A-B) being used to dehydrate a concentrated blood component (FIGS. 5C-D)
Figure 5B:
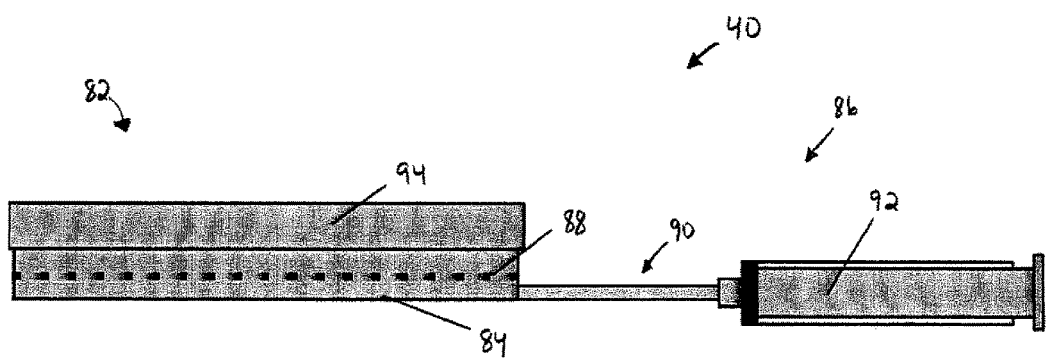

In another aspect, a desired amount of liquid (e.g., water) can be removed from the coagulated blood component 24 using a vacuum assembly 40 (FIGS. 5A-D). As shown in FIGS. 5A-B, the vacuum assembly 40 can generally comprise a housing 82 defining a receiving cavity 84 (not shown in detail) that is in fluid communication with a suction mechanism 86. In some instances, the housing 82 can include a mold 26 (FIGS. 2A-E) as described above. The receiving cavity 84 (FIGS. 5A-B) further includes a membrane 88 disposed therein. In some instances, the membrane 88 can be treated or coated with a coagulation activator, such as thrombin. The receiving cavity 84 is in fluid communication with the suction mechanism 86 via a conduit 90 (e.g., plastic tubing). In one example, the suction mechanism 86 can comprise syringe 92, such as a VacLok® vacuum syringe (Merit Medical, South Jordan, Utah).

Figure 5C:
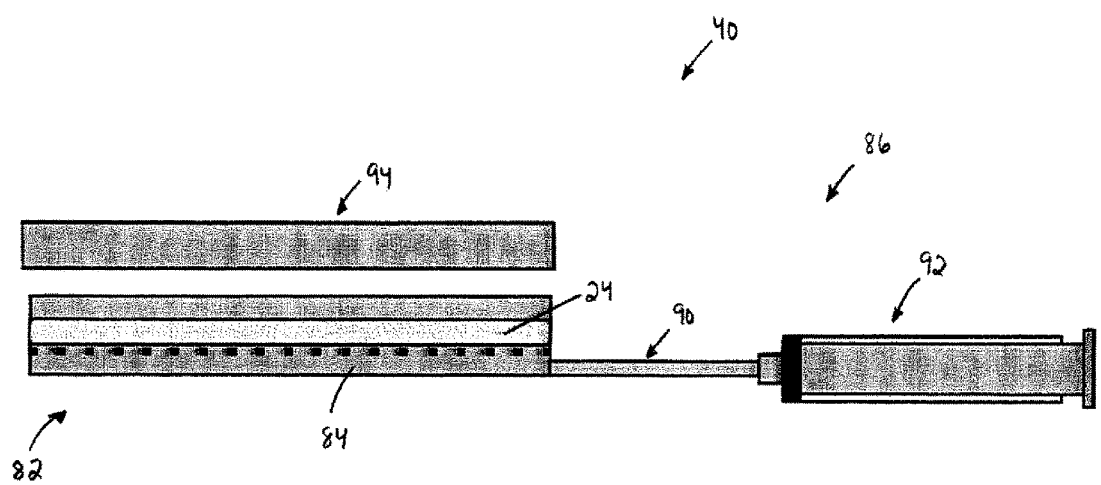
Figure 5D:
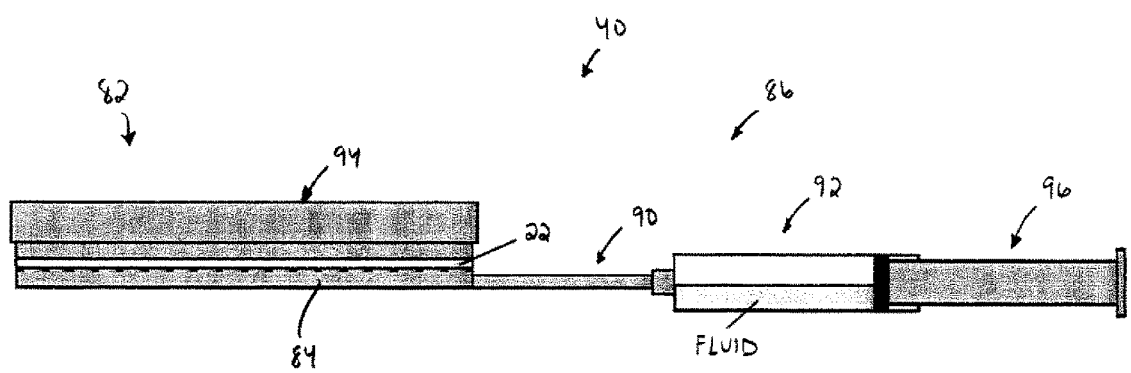

Operation of the vacuum assembly 40 is illustrated in FIGS. 5C-D. In some instances, a coagulated blood component 24 can be placed in the receiving cavity 84 so that the coagulated blood component contacts the membrane 88. In other instances, a blood component (e.g., a platelet component) can be placed in the receiving cavity 84 so that the blood component contacts a thrombin-coated membrane 88 and is thereby partially or completely clotted. After placing the blood component (or coagulated blood component 24) in the receiving cavity 84, a cap 94 can be placed over the housing 82 to seal the receiving cavity 84 (FIG. 5D). The suction mechanism 86 can then be activated to generate negative pressure in the receiving cavity 84, thereby causing liquid (e.g., water) to be removed from the blood component. Where the suction mechanism 86 comprises a VacLok® syringe 92, for example, tactile force can be used to retract the syringe plunger 96 and thereby create negative pressure in the receiving cavity 84. Creation of negative pressure causes liquid (e.g., water) to be removed from the blood component, which can travel through the membrane 88 and into the syringe 92 via the fluid conduit 90. After the blood component is dehydrated to the desired liquid (e.g., water) content, the resultant membrane 22 may be used for a desired biological application.

In another aspect, the multipurpose membrane 22 of the present disclosure can include one or more therapeutic additives. Therapeutic additives can be present in the material(s) (e.g., blood, bone marrow, etc.) used to prepare the membrane 22, added to the material(s) (and other components of the membrane) prior to or during formation of the membrane, and/or the membrane can be post-treated with a therapeutic additive (or additives) by, for example, coating with or immersion into a composition comprising the therapeutic additive(s).

A therapeutic additive can include any protein, glycoprotein, sugar, polysaccharide, lipid, DNA, RNA, aptamer, peptide, hormone, vitamin, cell, or any other such substance, which when introduced into a subject is capable of eliciting a biological response. Examples of therapeutic additives can include, but are not limited to: interleukins (IL), such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, isoforms thereof and others; interferons, such as interferon alpha, beta, gamma and others; growth factors, such as platelet derived growth factors (PDGF), acidic and basic fibroblast growth factors including FGF-1 and FGF-2, transformation growth factors beta (TGF-beta, e.g., TGF-beta-1, TGF-beta-2 and TGF-beta-3), insulin like growth factors (IGF, e.g., including IGF-I and IGF-II), epidermal growth factors (EGF, e.g., EGF and heparin binding EGF), platelet-derived angiogenesis factors (PDAF), platelet-derived endothelial growth factors (PDEGF), tumor necrosis factor-alpha (TNF-α), tumor necrosis factor-beta (TNF-β), vascular endothelial growth factors (VEGF), epithelial cell growth factors (ECGF), granulocyte-colony stimulating factors (G-CSF), granulocyte-macrophage colony stimulating factors (GM-CSF), nerve growth factors (NGF), neurotrophins, erythropoietin (EPO), thrombopoietin (TPO), myostatin (GDF-8), growth differentiation factor-9 (GDF9), hepatocyte growth factors (HGF), platelet factors, isoforms thereof, etc.; antibodies; bone morphogenetic proteins (BMPs), such as BMP-2, BMP-4, and BMP-7; extracellular matrix molecules, such as osteocalcin, osteonectin, fibrinogen, vitronectin, fibronectin, thrombospondin 1 (TSP-1), and bone sialoprotein (BSP); proteoglycans; metalloproteases or prometalloproteases and inhibitors thereof; angiotensin converting enzyme inhibitors; plasminogen and tissue plasminogen activators (TPA), including anisoylated plasminogen activator (TPA) and anisoylated plasminogen-streptokinase activator complex (APSAC), and inhibitors thereof; xymogens, such as prothrombin, plasminogen, prokallikrien, proelastase, and procollagenase; proteases, such as thrombin, plasmin, kallikrien, elastase, and collagenases; protease inhibitors, such as aprotinin, alpha 1-antitrypsin, alpha 2-microglobulin, alpha 2-antiplasmin, anti-thrombin and tissue inhibitor of metalloproteases (TIMP1); RNA and DNA in its various forms (e.g., to modify gene expression and function); cytokines including chemotactic cytokines (chemokine); protein-based hormones, such as parathyroid hormone; engineered hormones; steroid-based hormones, such as estrogen, pregnenolone, aldosterone, estradiol, cortisol, testosterone, progesterone, etc.; peptide hormones, such as insulin, parathyroid hormone related peptide, luteinizing hormone (LH), adrenocorticotropic hormone (ACTH), follicle stimulating hormone (FSH), and angiotensin II/III; synthetic steroids including, but not limited to, glucocorticoids, such as prednisone, dexamethasone, triamcinolone, etc.; mineralocorticoids, such as fludrocortisones; Vitamin D derivatives, such as dihydrotachysterol; synthetic androgens, such as oxandrolone, decadurabolin, etc.; synthetic estrogens, such as diethylstilbestrol (DES); synthetic progestins, such as norethindrone and medroxyprogesterone acetate; and mixtures thereof.

In other instances, a therapeutic additive can include a drug. The term "drug" can refer to a substance used as a medication or in the preparation of medication including, but not limited to, a substance intended for use in the diagnosis, cure, mitigation, treatment, or prevention of a condition, such as infection, disease or trauma. Non-limiting examples of drugs that may be used as a therapeutic additive can include small organic molecules, complex organic molecules, inorganic elements and molecules, and the like. Generally, the term "drug" can encompass fungicides, anticoagulants, antibiotics, antivirals, anti-inflammatories (both steroidal and non-steroidal), antibodies, and other molecules. Examples of suitable drugs can include, but are not limited to: analgesics; anti-infective agents, such as antibiotics (e.g., cephalosporins, penicillins, aminoglycosides including gentamicin and neomycin, glycopeptides including vancomycin, macrolides including, but not limited to, azithromycin and clarithromycin, quinolones including ciprofloxacin, gatifloxacin, and levofloxacin, sulfonamides; and tetracycline), antifungals (e.g., polyene antifungals, imidazole antifungals and triazole antifungals), and antivirals; antineoplastics, such as antibiotics, antimetabolites, hormonal agonists/antagonists, androgens, immunomodulators, skin and mucous membrane agents and steroids; biologicals; blood modifiers, such as anticoagulants, antiplatelet agents, colony stimulating factors, hematinics, hemorrheologic agents, hemostatics, thrombin inhibitors and thrombolytic agents; cardioprotective agents; cardiovascular agents, such as adrenergic blockers, adrenergic stimulants, angiotensin converting enzyme (ACE) inhibitors, angiotensin II receptor antagonists, antiarrhythmics, antilipemic agents, beta adrenergic blocking agents, vasodilators, and vasopressors; cholinesterase inhibitors; hormones, such as anabolic steroids, androgens, estrogens and combinations, glucocorticoids and growth hormone; immunomodulators; immunosuppressives; ophthalmic preparations, such as antibiotics, anti-infectives, anti-inflammatory agents and beta adrenergic blocking agents; respiratory agents, such as anti-infective agents, anti-inflammatory agents, skin and mucous membrane agents, anti-cancer agents; and mixtures thereof.

In other instances, a therapeutic additive can include a cell, such as an autologous, allogeneic, or xenogenic stem cell. Stem cells can be embryonic or adult. In one example, stem cells can be seeded onto or within the membrane 22 by dispersing the stem cells on top of the membrane or soaking the membrane in a composition comprising the stem cells.

The presence and/or amount of a therapeutic additive (or additives) present in the membrane 22 can be determined by assays and analytical methods well known to those skilled in the art. A drug, for example, can be administered via the membrane 22 in a therapeutically effective amount, i.e., that amount of a pharmacological or therapeutic agent that will elicit a biological or medical response of a tissue, system, or subject that is being sought by the administrator (e.g., a researcher, physician, clinician or veterinarian). A biological or medical response can include alleviation of the symptoms of a condition or disease being treated and/or the prevention, slowing, or halting of progression of the condition or disease.

It will be appreciated that the membrane 22 can be preferentially shaped following formation. For example, membranes 22 of the present disclosure can be post-fabricated to possess one or more desired mechanical properties related to a desired biological application. A "mechanical property" can refer to essentially any property that provides some description for how a substance responds to the application of an external force. Exemplary mechanical properties can include tensile strength, compression strength, flexural strength, impact strength, elongation, elasticity, stiffness and toughness. In some instances, one or more membranes 22 of the present disclosure can be stacked or laminated into layers of films, sheets or tubular rolls. In other instances, one or more membranes 22 of the present disclosure can be in the form of a bone substitute, a cartilage substitute, a tendon substitute, a ligament substitute, a skin substitute, a cornea substitute, a stent, a fixation plate, a screw, a suture or a staple. In further instances, membranes 22 of the present disclosure can have different physical or chemical characteristics within each membrane, such as a gradient or multiple gradients of therapeutic additives and/or physical characteristics (e.g., density, porosity, elasticity and/or tensile strength).

Figure 6:
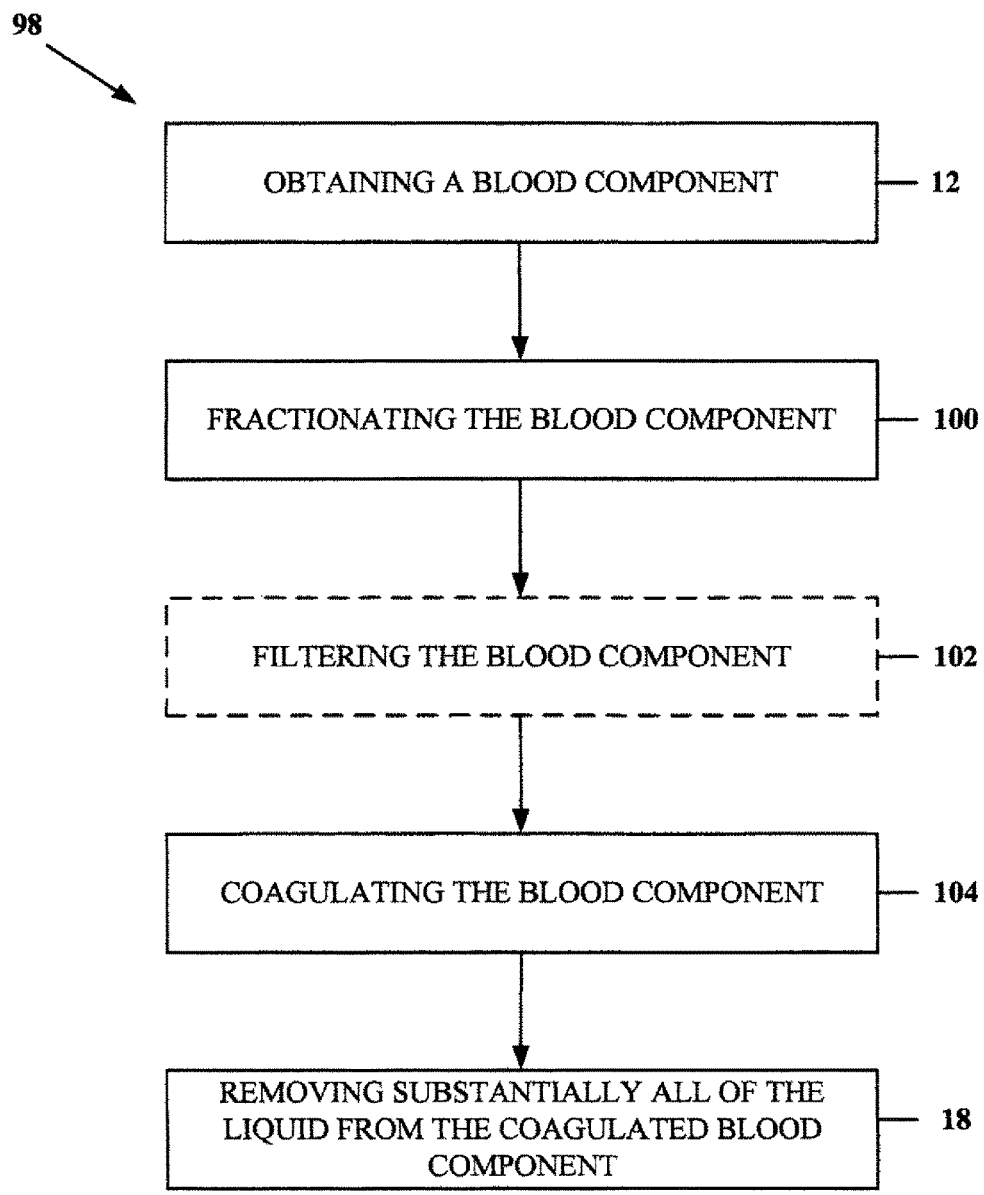
FIG. 6 is a process flow diagram illustrating a method of forming a membrane for a hemostatic application according to another aspect of the present disclosure.

Another aspect of the present disclosure is illustrated in FIG. 6 and includes a method 98 of forming a multipurpose membrane (not shown) for a hemostatic application. Non-limiting examples of hemostatic applications can include treatment of wounds caused by trauma or surgery. The method 98 is similar to the method 10 (FIG. 1) described above. Therefore, steps that are identical to those in FIG. 1 will use the same reference numbers, whereas steps that are different will use different reference numbers.

The method 98 can begin by first obtaining one or a combination of blood components (e.g., whole blood) (Step 12). In some instances, the blood component(s) can be obtained from a subject who will receive (e.g., be treated with) a multipurpose membrane. In other words, the blood component(s) used for the method 98 will be autologous. At Step 100, the blood component(s) can be fractionated using, for example, a centrifuge to obtain a desired component thereof (e.g., a platelet component). The fractionated blood component(s) can then be optionally filtered (e.g., using an ultrafiltration membrane) (Step 102). After fractionating the blood component(s), the fractionated component(s) can be contacted with a coagulation activator to partially or completely clot the fractionated component(s) (Step 104). At Step 18, a desired amount of liquid (e.g., water) can be removed from the coagulated blood component(s). For example, a wicking assembly 38 or a vacuum assembly 40 can be used (as described above) to remove liquid (e.g., water) from the coagulated blood component(s). After dehydrating the coagulated blood component(s), the resultant membrane may be used for a desired hemostatic application.

Biological Applications

In another aspect, multipurpose membranes 22 of the present disclosure can find use in a variety of biological applications. As such, multipurpose membranes 22 of the present disclosure can be biocompatible and biodegradable. In some instances, multipurpose membranes 22 are biocompatible with the subject upon whom the membrane is intended to be contacted or implanted. The term "biocompatible" can refer to the absence of stimulation of a severe, long-lived, escalating, contrary, or adverse biological response to an implanted membrane 22, and is distinguished from a mild, transient inflammation that typically accompanies surgery or implantation of an acceptable biocompatible material into a living organism. In other instances, multipurpose membranes 22 can be biodegradable or bioerodible, e.g., degradable in response to certain proteolytic processes. As used herein, the terms "biodegradable" and "bioerodible" can refer to the dissolution of a substance (e.g., a multipurpose membrane 22) into constituent parts that may be metabolized or excreted under the conditions normally present in a living tissue. In certain aspects, the rate and/or extent of biodegradation or bioerosion can be controlled in a predictable manner.

In some aspects, multipurpose membranes 22 of the present disclosure may be fabricated for short-term (e.g., acute), long-term, or permanent implantation into (or onto) a subject. For example, a membrane 22 may be used to repair or replace diseased or damaged tissue or portions of an organ (e.g., liver, bone, heart, etc.). In other aspects, a membrane 22 can be biodegradable and form a temporary structure. For instance, a bone fracture may be temporarily repaired with a membrane 22 that will undergo controlled biodegradation occurring concomitantly with bioremodeling by the host's cells. In further instances, the membrane 22 can be less biodegradable to provide more permanent grafts or replacements.

Multipurpose membranes 22 of the present disclosure may be useful for a variety of biological applications including, but not limited to: wound or tissue repair; tissue grafts, such as bone grafts, tendon grafts, ligament grafts, or skin grafts; nerve guides; protection of dura; prosthetics/tissue interfaces; corneal grafts; plates; screws; fixtures; guides; sutures; clips; staples; barbs; resurfacing materials; tendon or ligament repair; and scaffolds for tissue engineering (e.g., for cell delivery, such as stem cell delivery). As used herein, the term "wound" can refer to any detectable break in the tissues or bones of the body, such as injury to skin or to an injury or damage, or to a damaged site associated with a disease or disorder. In some instances, for example, the term "wound" can relate to a physical tear, break, or rupture to a tissue or cell layer. In other instances, a wound may occur by any physical insult, including a surgical procedure or as a result of a disease, disorder condition. Examples of wound types for which the multipurpose membrane 22 may be used can include, but are not limited to, skin wounds, ocular wounds, burn wounds, chronic wounds, and ulcers. Additional examples of wounds can include wounds caused by laser surgery, chemical burns, cancer treatments, biopsy excision sites, and scars from pathogens, gunshot or knife stabbings, cosmetic surgery and reconstructive surgery.

In one example, multipurpose membranes 22 of the present disclosure can be used to create bioresorbable wound dressings or band-aids. Wound dressings may be used as a wound-healing dressing, a tissue sealant (i.e., sealing a tissue or organ to prevent exposure to a fluid or gas, such as blood, urine, air, etc., from or into a tissue or organ), and/or a cell-growth scaffold. In some instances, the wound dressing may protect the injured tissue, maintain a moist environment, and be water permeable, easy to apply, not require frequent changes, be non-toxic, be non-antigenic, maintain microbial control, and/or deliver effective healing agents to the wound site. Wound dressings may be used in conjunction with wound repair applications, such as: orthopedic applications (e.g., bone filling/fusion for osteoporosis and other bone diseases); cartilage repair for arthritis and other joint diseases; tendon repair; soft tissue repair, including nerve repair, organ repair, skin repair, vascular repair and muscle repair; and ophthalmic applications. In other instances, wound dressings may be used in association with any medical condition that requires coating or sealing of a tissue, examples of which can include: sealing lung tissue against air leakage after surgery; avoiding or mitigating undesirable adherence between a wound and another material (e.g., to prevent scar adhesion to a repair site); preventing or reducing leakage of blood, serum, urine, cerebrospinal fluid, air, mucus, tears, bowel contents, or other bodily fluids; preventing post-surgical adhesions, including those of the pelvis and abdomen, pericardium, spinal cord and dura (e.g., using a multipurpose membrane 22 as packing over a nerve root or roots during spinal surgery), tendon, and tendon sheath; treating exposed skin; repairing or healing of incisions, abrasions, burns, inflammation, and other conditions requiring application of a coating to the outer surfaces of the body; applying coatings to other body surfaces, such as the interior or exterior of hollow organs, including blood vessels (e.g., microvascular and/or macrovascular structures to repair and improve vessel patency and mitigate or prevent repair site leakage), cardiovascular surgery applications, thoracic surgery applications, neurosurgery applications and general surgery applications; repair in general trauma, plastic surgery applications (e.g., craniofacial applications), ophthalmic applications, orthopedic surgery applications and gynecology/obstetrics applications; urology applications; dental surgery applications (e.g., treating TMJ); and repair of incisions and other openings made for surgical purposes.

In another example, a multipurpose membrane 22 formed by the method 10 of FIG. 1 can be used to repair a damaged peripheral nerve. As discussed above, conventional nerve repair techniques include the use of sutures and/or fibrin glue. When such techniques are used, nerves typically regenerate across the repair site in an exuberant manner with regenerating axons aberrantly growing out from the repair site, which leads to fewer axons entering the distal nerve stump towards the denervated target and undesirable nerve scar (neuroma) formation about the repair site. Advantageously, one aspect of the present disclosure can include applying a multipurpose membrane 22 to a damaged peripheral nerve, such as a severed peripheral nerve. The multipurpose membrane 22 can be formed as surgical sheet or roll that may be wrapped about the opposing severed ends of the peripheral nerve. The multipurpose membrane 22 can additionally include one or more therapeutic additives (e.g., stem cells and/or growth factors) to further promote nerve regeneration and/or prevent excess scar formation. Different therapeutic additives can be applied to each side of the multipurpose membrane 22 for different purposes (e.g., on an outside or outwardly-facing surface to prevent scar adhesion to the repair site and on an inside or inwardly-facing surface to promote nerve regeneration). The multipurpose membrane 22 can be wrapped around the damaged nerve so as to envelop both of the severed ends. On account of the membrane's durability, sutures can be used to anchor the membrane 22 about the damaged nerve. The membrane 22 can then remain in the body long enough to augment the initial healing response, minimizing scarring, and promote regeneration and/or revascularization.

Hemostatic Devices and Methods

Figure 7:
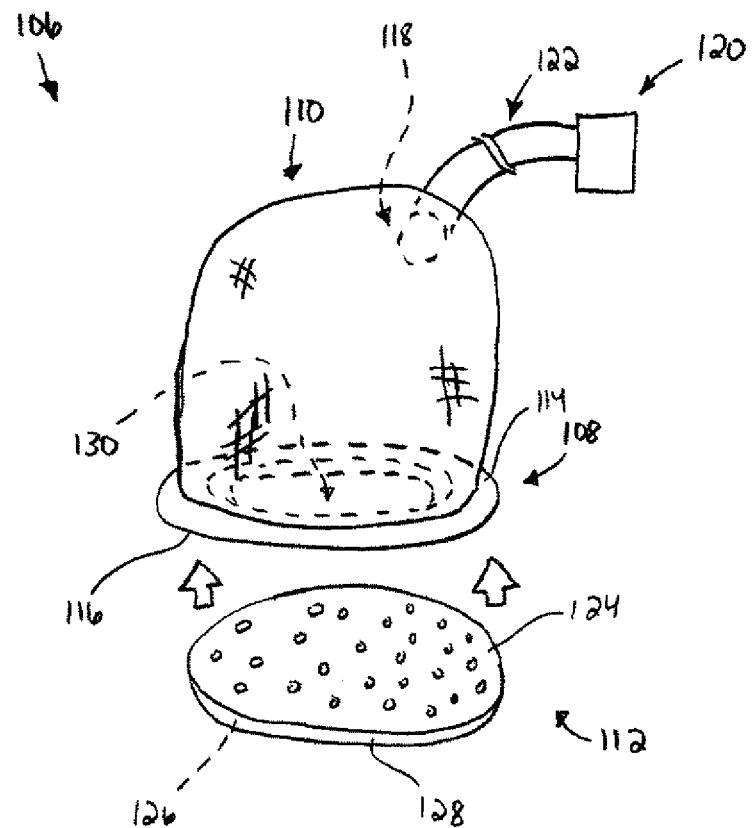
FIG. 7 is a perspective view showing a pressured hemostatic device constructed in accordance with another aspect of the present disclosure.

Another aspect of the present disclosure is illustrated in FIG. 7 and includes a pressurized hemostatic device 106 to promote accelerated healing of a wound. Generally, the device 106 facilitates the flow of a therapeutic gas over a wound to evaporate water and aid in the clotting mechanism. The pressure and/or temperature of the therapeutic gas can be regulated to help increase evaporation. Advantageously, the pressure of the therapeutic gas itself may be used to contain bleeding at a desired boundary (e.g., by equalizing the pressure of the therapeutic gas with the pressure of blood exiting the wound), thereby resulting in a gas pressure "bandage" until hemostasis can occur. The pressurized hemostatic device 106 avoids the detrimental effect of using direct pressure (e.g., gauze), which can lead to tearing of clot and continued bleeding upon removal. As described in more detail below, the pressurized hemostatic device 106 can have various configurations to accommodate different wound sites and different wound dimensions.

As shown in FIG. 7, the pressurized hemostatic device 106 can comprise an elastic collar 108, a gas container 110 operably connected to the collar, and an optional gas permeable membrane 112. The elastic collar 108 is malleable, which enables the collar to conform to the shape of a subject's body where a wound is located so that a seal can be formed between the collar and the subject's skin. The gas container 110 is operably connected to the elastic collar 108, and is configured to direct a therapeutic gas through the elastic collar toward a wound to automatically mold the membrane 112. The elastic collar 108 includes oppositely disposed upper and lower portions 114 and 116. The elastic collar 108 can be configured to encircle a wound. In one example, the elastic collar 108 can have a circular or elliptical shape; however, it will be appreciated that the collar can have any shape depending upon the dimensions of the wound. The elastic collar 108 can be made of any one or combination of biocompatible materials, such as silicon, PTFE, rubber, etc. The elastic collar 108 can optionally include one or more connectors (e.g., Velcro, snaps, clips, mild adhesive, an adjustable arm including, for example, a rod with one or more joints, etc.) (not shown) to facilitate attachment of the pressurized hemostatic device 106 to a subject.

The upper portion 114 of the elastic collar 108 is operably connected to the gas container 110 so that a fluid tight seal is formed there between. In some instances, the gas container 110 can comprise a gas bladder configured to retain one or a combination of pressurized therapeutic gases. Generally, therapeutic gases that may be retained in the gas container 110 can include any gas capable of promoting both evaporation and hemostasis. In one example, the therapeutic gas can include carbon dioxide. In another example, the therapeutic gas can include oxygen. The gas container 110 can have a flexible or semi-flexible configuration. The gas container 110 can be made of any suitable material(s) capable of retaining the therapeutic gas. In one example, the gas container 110 can comprise a plastic bag. The size (e.g., volume) of the gas container 110 can be varied depending upon the type and nature of the wound. A large wound, for example, may require a gas container 110 having a volume of greater than about 1 L, while a smaller wound may require a gas container having a volume of less than about 1 L.

The gas container 110 can include at least one outlet 118 in fluid communication with a control mechanism 120. The control mechanism 120 can be configured to adjust the temperature and/or pressure of the therapeutic gas within the gas container 110. In some instances, the outlet 118 can be connected to the control mechanism 120 via plastic tubing 122. In other instance, the control mechanism 120 can include a pressurized therapeutic gas source (not shown), such as a tank or other container. In further instances, the control mechanism 120 can include a temperature regulator or adjustor (not shown). In one example, a heater unit (not shown) can increase the temperature and/or a cooling unit (not shown) can diminish the temperature of the pressurized gas for improved healing and/or comfort. The temperature regulator or adjuster can include controls for modifying the temperature and/or sensors for measuring the subject's skin temperature and/or the ambient temperature. The control mechanism 120 can also comprise a timer (not shown) for determining the amount of time that the pressurized hemostatic device 106 has been applied to a subject. The timer can include an audible or visual indicator or an automatic shut off after a specified period of time.

The gas permeable membrane 112 is configured to operably mate with the collar 108. The gas permeable membrane 112 includes oppositely disposed first and second surfaces 124 and 126. A mating portion (not shown in detail) of the first surface 124 is configured to operably mate with the lower portion 116 of the elastic collar 108. In some instances, the mating portion can include a perimeter of the first surface 124 so that the perimeter is flush against the lower portion 116 of the collar 108 when the collar is mated with the gas permeable membrane 112. In other instances, the mating portion can include an outer edge 128 of the gas permeable membrane 112. In this instance, the gas permeable membrane 112 can be configured to snugly fit within the central opening 130 of the elastic collar 108. In one example, the gas permeable membrane 112 can be made of a compressive and resilient material (e.g., foam or gauze), enabling the membrane to conform to the shape of the subject's body where the wound is located so that substantially all of the second surface 126 can contact the wound. In another example, the gas permeable membrane 112 can comprise a multipurpose membrane 22 of the present disclosure. In some instances, the second surface 126 of the gas permeable membrane 112 can be planar as shown in FIG. 7. Alternatively, the second surface 126 of the gas permeable membrane 112 can be shaped to fit a particular area of the subject's body, such as an elbow, foot, etc. In some instances, the gas permeable membrane 112 is free of any exogenously-added therapeutic agents.

The pressurized hemostatic device 106 can be configured for use in a stationary setting, such as in a hospital room (e.g., bedside). Alternatively, the pressurized hemostatic device 106 can be configured to be portable and/or worn by a subject. In such instances, a portable device 106 can further include an attachment structure (not shown), such as an elastic sock, sleeve or sheath. Further, a device 106 configured for portable use may include a portable power supply (e.g., a rechargeable battery) (not shown), a portable gas supply (e.g., a compressed gas tank) (not shown), and/or a gas generator (not shown).

Figure 8A:
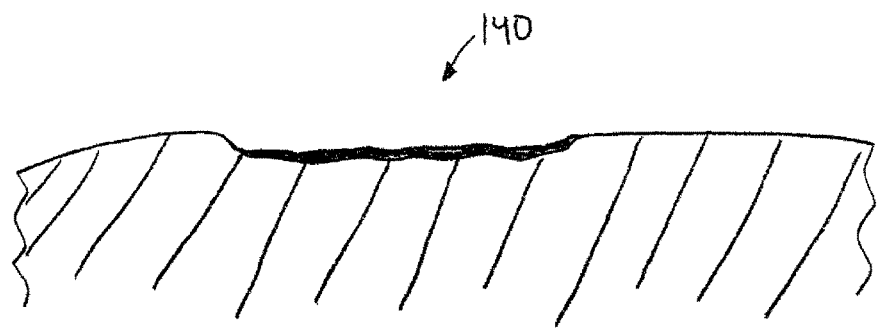
FIGS. 8A-B are a series of schematic illustration showing a method for promoting hemostasis of a wound according to another aspect of the present disclosure.
Figure 8B:
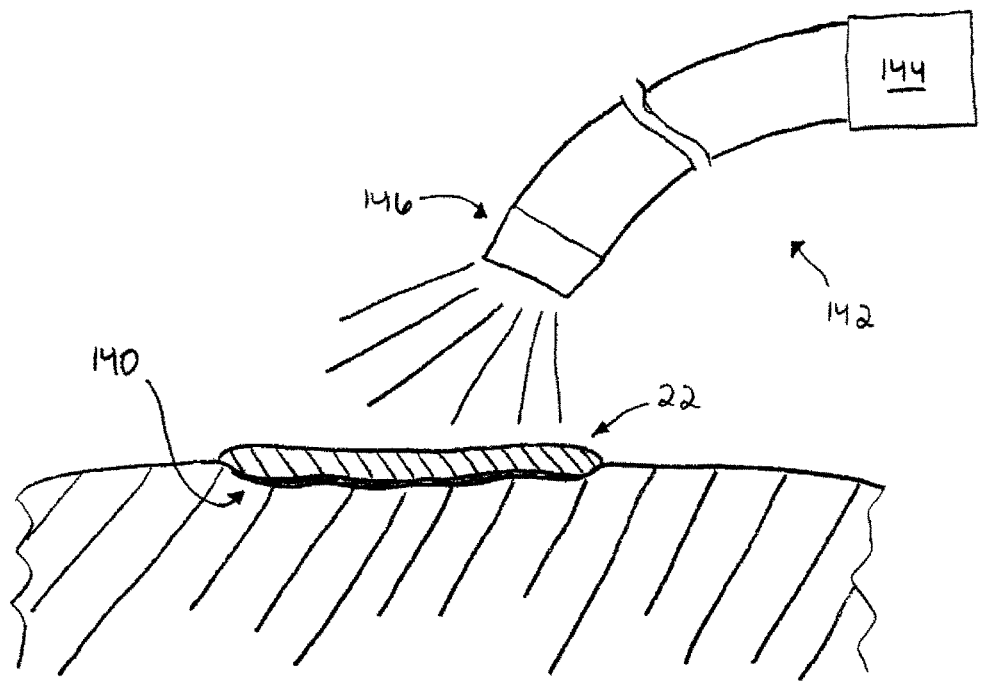

Another aspect of the present disclosure is illustrated in FIGS. 8A-B and includes a method for promoting hemostasis of a wound 140 (FIG. 8A). One step of the method can include contacting a multipurpose membrane 22 (FIG. 8B)

with at least a portion of the wound 140. In one example, the multipurpose membrane 22 can be applied to a skin wound (e.g., an ulcer) so that the entire wound is covered by the multipurpose membrane. After applying the multipurpose membrane 22 to at least a portion of the wound 140, a therapeutic gas (indicated by splayed lines) can be applied to all or only a portion of the multipurpose membrane in an amount and for a time sufficient to promote hemostasis of the wound (e.g., the portion of the wound in contact with the multipurpose membrane). Examples of a therapeutic gas are described above.

Figure 9A:
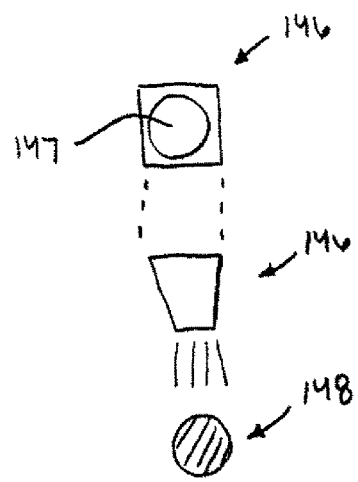
FIGS. 9A-C are a series of schematic illustrations showing various nozzle configurations for use with the method in FIGS. 8A-B.
Figure 9B:
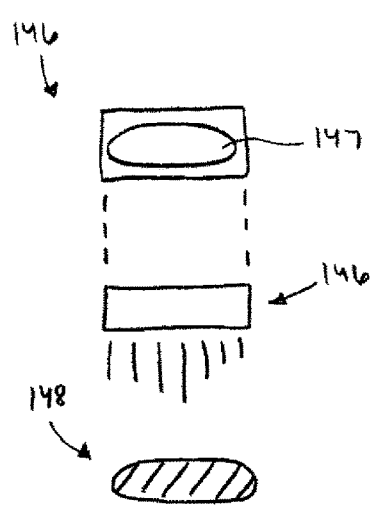
Figure 9C:
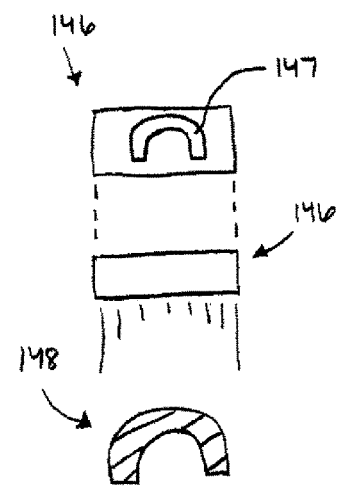

As shown in FIG. 8B, the therapeutic gas can be applied to the multipurpose membrane 22 by a gas conduit 142. The gas conduit 142 can comprise any mechanism that is operably connected to one or more therapeutic gas sources 144 (e.g., a pressurized tank) and is capable of selectively dispensing the therapeutic gas. In some instances, the gas conduit 142 can comprise a malleable or articulating arm configured to selectively pass a therapeutic gas therethrough. In other instances, the gas conduit 142 can comprise a handheld gun or dispenser configured to selectively dispense the therapeutic gas. As shown in FIG. 8B, the gas conduit 142 can further include a distal end 146 configured to dispense the therapeutic gas in a pre-determined spray pattern 148 (FIGS. 9A-C). In some instances, the distal end 146 can comprise a cap or nozzle having at least one channel 147 with a cross-sectional shape configured to emit a pre-determined spray pattern 148 during operation of the gas conduit 142. As shown in FIGS. 9A-C, a channel 147 comprising the distal end 146 can have, for example, a circular cross-sectional shape (FIG. 9A), an elliptical cross-sectional shape (FIG. 9B), or a horseshoe-shaped cross-sectional shape (FIG. 9C).

Figure 10A:
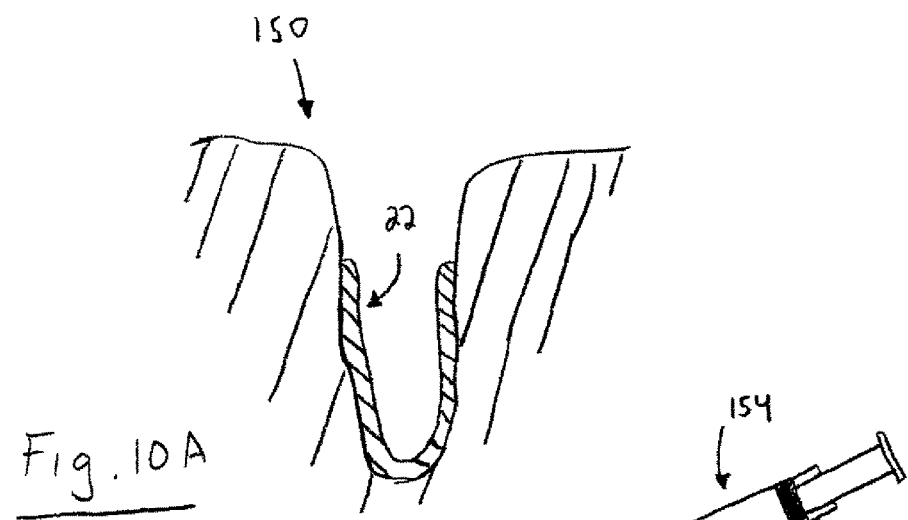
FIGS. 10A-C are a series of schematic illustration showing a method for promoting hemostasis of a deep wound according to another aspect of the present disclosure.
Figure 10B:
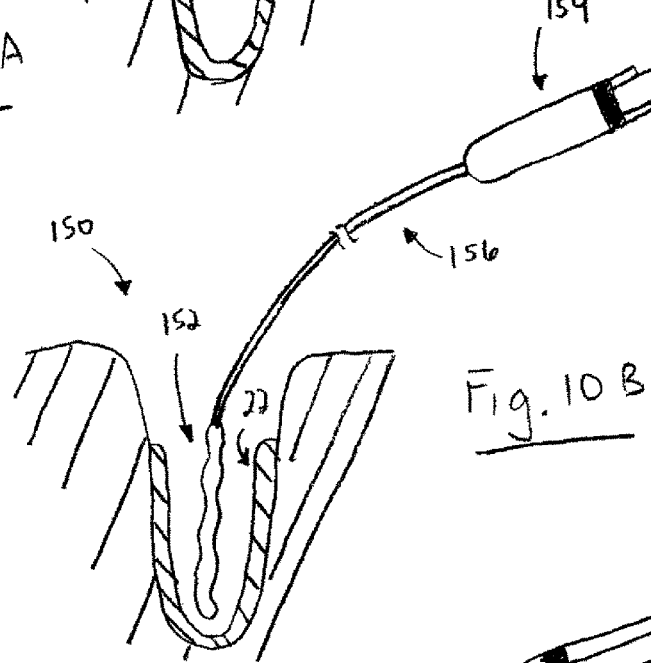
Figure 10C:
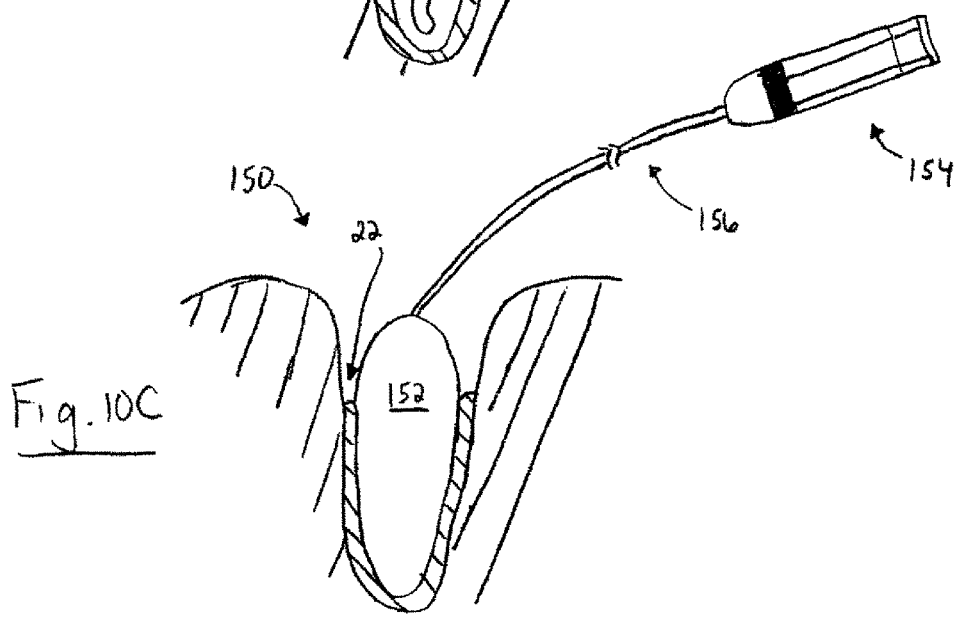

Another aspect of the present disclosure is illustrated in FIGS. 10A-C and includes a method for promoting hemostasis of a deep wound 150. In one example, a deep wound 150 (FIG. 10A) can include any puncture or tear in the skin that extends at least through the epidermis. One step of the method can include providing an inflatable member 152 (FIG. 10B). In some instances, the inflatable member 152 can include a balloon. The inflatable member 152 can be in fluid communication with a pressure source 154, such as a syringe. As shown in FIG. 10B, the pressure source 154 can be connected to the inflatable member 152 via a fluid conduit 156, such as medical tubing. As described in more detail below, the inflatable member 152 can be used in conjunction with the multipurpose membrane 22 to promote hemostasis by applying mechanical pressure to the wound 150 and thereby stabilizing the multipurpose membrane within the wound.

Operation of the inflatable member 152 in conjunction with a multipurpose membrane 22 is illustrated in FIGS. 10A-C. Although operation of the inflatable member 152 with a multipurpose membrane 22 is shown in FIGS. 10A-C, it will be appreciated that the inflatable member can be used without a multipurpose membrane to apply mechanical pressure to a deep wound 150 and thereby promote hemostasis. As shown in FIG. 10A, a multipurpose membrane 22 can first be placed into a deep wound 150 to cover substantially the entire wound. Alternatively, the multipurpose membrane 22 can be placed about the inflatable member 152 and then delivered into the wound 150. Once the multipurpose membrane 22 is positioned in the wound 150, the inflatable member 152 is inserted into the wound as shown in FIG. 10B. With the inflatable member 152 positioned adjacent the multipurpose membrane 22, the pressure source 154 can be actuated (e.g., by depressing the handle of a syringe) to infuse an inflation medium (e.g., air or saline) into the inflatable member. As shown in FIG. 10C, the inflatable member 152 is then inflated so that the inflatable member expands into flush contact with the multipurpose membrane 22, thereby applying mechanical pressure to the wound 150 while also stabilizing the multipurpose membrane. The inflatable member 152 can then be deflated and removed for wound closure. It will be appreciated that the multipurpose membrane 22 can additionally or optionally be stabilized using tacks, sutures, or the like.

In another aspect, the inflatable member 152 can additionally or alternatively include a drain mechanism (not shown) configured to continuously or periodically remove fluid (e.g., serous fluid) from a wound 150 during operation of the inflatable member. For example, the drain mechanism can include a drain conduit that extends axially from a distal end (not shown in detail) of the fluid conduit 156 through the inflatable member 152. The drain conduit can further include an open distal end configured to apply suction and remove fluid from the wound 150. It will be appreciated that the drain conduit can include one or more hollow vein members that extend radially from the drain conduit into communication with the wound 150. Such hollow vein members can increase the total effect surface area available for fluid suction from the wound 150. During operation, the inflatable member 152 can be inflated (as described above) to stabilize the multipurpose membrane 22 and maintain pressure on the walls of the wound 150. Simultaneously, the drain mechanism can be operated to remove fluid from the wound 150 and prevent unwanted fluid build-up during use. Following successful application of the multipurpose membrane 22, the inflatable member 22 can be deflated and removed (along with the drain mechanism) in a manner similar to any post-operative procedure.

Figure 11:
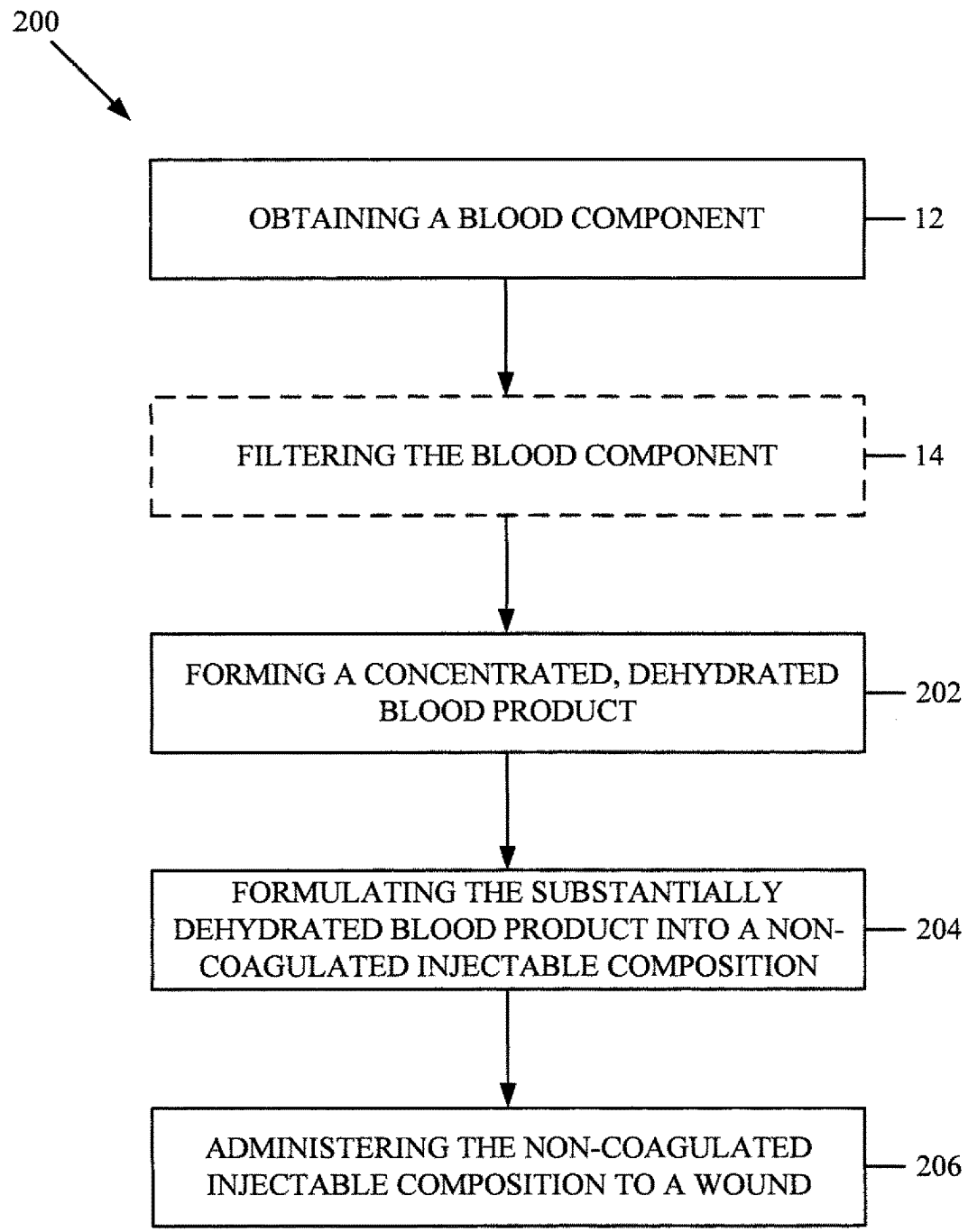
FIG. 11 is a process flow diagram illustrating a method for forming a multipurpose membrane in vivo according to another aspect of the present disclosure.

Another aspect of the present disclosure is illustrated in FIG. 11 and includes a method 200 for forming a multipurpose membrane (not shown) in vivo. Certain steps of the method 200 are similar to the methods 10 and 98 (FIG. 1 and FIG. 6, respectively) described above. Therefore, steps that are identical to those in FIG. 1 and FIG. 6 will use the same reference numbers, whereas steps that are different will use different reference numbers. Unlike the methods 10 and 98 described above, the method 200 does not entail forming a multipurpose membrane ex vivo. Rather, as described in more detail below, the method 200 entails forming a non-coagulated, injectable composition that is transformed into a multipurpose membrane upon contact with one or more coagulation factors associated with a wound. Consequently, the method 200 presents several advantages including, but not limited to, providing an injectable composition that can be easily transported and applied in various settings (e.g., in a surgical ward, on a battlefield, etc.) to a wound (or wounds) of varying size, shape and severity.

As shown in FIG. 11, the method 200 can begin by first obtaining one or a combination of blood components (e.g., bone marrow) (Step 12). In some instances, the blood component can be obtained from a subject who will receive (e.g., be treated with) an injectable composition. In other words, the blood component used for the method 200 can be autologous. In other instances, the blood component can be fractionated using, for example, a centrifuge to obtain a desired component or fraction thereof. The blood component can then be optionally filtered (e.g., using an ultrafiltration membrane) (Step 14).

At Step 202, a desired amount of liquid (e.g., water) can be removed from the coagulated blood component to form a concentrated, substantially dehydrated blood component.

For example, a vacuum assembly 40 can be used (as described above) to remove liquid (e.g., water) from the blood component. Either prior to or following Step 202, the blood component (or the substantially dehydrated blood component) can be subject to centrifugation to concentrate the blood component (or the substantially dehydrated blood component). In some instances, one or more therapeutic agents (e.g., antibiotics, antifibrolytics, or any of those listed above) can be contacted with the blood component prior to, or contemporaneous with, Step 202.

After forming the substantially dehydrated blood component, the substantially dehydrated blood component can be formulated into a non-coagulated injectable composition (Step 204). The phrase "injectable" or "injectable composition" can refer to a composition that is prepared according to the method 200 and can be drawn into a dispensing device (e.g., a syringe, a sterile packet, a pouch, etc.) and be injected into, or spread about, a wound without causing adverse effects due to the presence of solid material(s) in the composition. Solid materials that may be present in the injectable composition can include, but are not limited to, crystals, gummy masses and gels. In one example of the present disclosure, the substantially dehydrated blood component can be formulated into a gelled injectable composition. In some instances, a formulation or composition is considered to be injectable when no more than about 10%, no more than about 5%, no more than about 2%, and no more than about 1% of the formulation is retained on a filter when the composition is filtered through the filter at about 98° F. It will be appreciated that one or more therapeutic agents (e.g., antibiotics, antifibrolytics, or any of those listed above) can be contacted with the injectable composition before the composition is administered to a wound. After formulating the injectable composition, a desired volume of the composition can be placed in the dispensing device for future use.

At Step 206, the injectable composition can be administered to a wound of the subject. Examples of wounds to which the injectable composition may be administered are illustrated above. Additional examples of wounds into or onto which the injectable composition can be administered include tendons, ligaments, cartilage, fat, muscles, and any void or cavity within a bodily tissue or bone (e.g., an intra-articular space). The amount of the injectable composition administered to the wound will depend upon the dimensions and severity of the wound. In some instances, an amount of the injectable composition can be injected directly into a wound so as to completely cover the wound surface, but not entirely fill the wound volume and thereby cover the entire wound surface. In other instances, an amount of the injectable composition can be injected directly into a wound so as to completely fill the wound volume. In further instances, an amount of the injectable composition can be injected directly into a wound as well as one or more surfaces surrounding the wound.

Upon administering the injectable composition to the wound, the multipurpose membrane is formed by contacting one or more coagulation factors associated with the wound. Non-limiting examples of coagulation factors that may be associated with the wound can include various components of plasma involved in the coagulation of blood, including fibrinogen, prothrombin and calcium ions. If desired, exogenous coagulation activators (such as those listed above) can be contacted with the injectable composition following administration of the injectable composition to the wound. Advantageously, coagulation of the injectable composition (and thus formation of the multipurpose membrane in or about the wound) provides a therapeutic seal about the exposed wound surface to promote increased wound healing.

From the above description of the present disclosure, those skilled in the art will perceive improvements, changes and modifications. For example, it will be appreciated that a gas and/or cryoprecipitation can be used to dehydrate a coagulated blood component 24. Additionally, it will be appreciated that formation of the multipurpose membrane 22 may done at a temperature that is greater than, equal to, or less than room temperature (or body temperature) (e.g., depending upon the type(s) of therapeutic agent(s) added to the membrane). Such improvements, changes, and modifications are within the skill of those in the art and are intended to be covered by the appended claims. All patents, patent applications, and publication cited herein are incorporated by reference in their entirety.

The following is claimed:

1. An ex vivo method for forming a multipurpose membrane, the method comprising the steps of:
   obtaining a volume of whole blood;
   contacting the volume of whole blood with an amount of thrombin and a source of calcium ions to form a coagulated whole blood component;
   placing the coagulated whole blood component in a wicking assembly;
   removing a liquid from a first surface of the coagulated whole blood component; and
   removing a liquid from an oppositely disposed, different second surface of the coagulated whole blood component;
   wherein removing liquid from the first and second surfaces results in the coagulated whole blood component having a water content of less than about 10%.

2. The method of claim 1, wherein the coagulated whole blood component is autologous, allogeneic or xenogeneic.

3. The method of claim 1, wherein the whole blood is subjected to ultrafiltration before contacting the whole blood with the thrombin and the source of calcium ions.

4. The method of claim 1, wherein the step of operating a vacuum assembly further comprises the steps of:
   providing a vacuum assembly comprising a housing having a receiving portion in fluid communication with a suction mechanism;
   disposing the coagulated whole blood component in the receiving portion; and
   operating the suction mechanism to generate a negative pressure within the receiving portion and thereby remove substantially all of the liquid from the coagulated whole blood component.

5. The method of claim 1, wherein the placing step further comprises pouring the coagulated white blood component into a mold.

6. The method of claim 1, being performed at about room temperature.

7. The method of claim 1, wherein the membrane is formed in less than about 30 minutes.

8. The method of claim 1, further including the step of imbibing the membrane with one or more therapeutic agents.

9. The method of claim 1, wherein the coagulated whole blood component is fully coagulated after the contacting step.

10. The method of claim 1, wherein only operation of the wicking assembly is performed to remove the liquid from the coagulated whole blood component.

11. An ex vivo method for forming a multipurpose membrane, the method consisting of:
- obtaining a volume of whole blood;
- contacting the volume of whole blood with an amount of thrombin and a source of calcium ions to form a coagulated whole blood component;
- placing the coagulated whole blood component in a wicking assembly;
- removing a liquid from a first surface of the coagulated whole blood component; and
- removing a liquid from an oppositely disposed, different second surface of the coagulated whole blood component;
- wherein removing liquid from the first and second surfaces results in the coagulated whole blood component having a water content of less than about 10%.

* * * * *